(12) United States Patent
Genberg et al.

(10) Patent No.: US 9,155,746 B2
(45) Date of Patent: Oct. 13, 2015

(54) COMPOSITIONS AND METHODS FOR TREATING BONE DISEASES AND BROKEN BONES

(75) Inventors: Carl Genberg, Las Vegas, NV (US); Paul B. Savage, Mapleton, UT (US)

(73) Assignee: Brigham Young University, Provo, UT (US)

( * ) Notice: Subject to any disclaimer, the term of this patent is extended or adjusted under 35 U.S.C. 154(b) by 164 days.

(21) Appl. No.: 13/615,244

(22) Filed: Sep. 13, 2012

(65) Prior Publication Data

US 2013/0243842 A1 Sep. 19, 2013

Related U.S. Application Data

(60) Provisional application No. 61/534,185, filed on Sep. 13, 2011.

(51) Int. Cl.
| | |
|---|---|
| A61K 8/02 | (2006.01) |
| A61K 31/575 | (2006.01) |
| A61K 45/06 | (2006.01) |
| A61K 38/18 | (2006.01) |

(52) U.S. Cl.
CPC ........... *A61K 31/575* (2013.01); *A61K 38/1875* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,661,341 A | 4/1987 | Benedict et al. | |
| 4,842,593 A | 6/1989 | Jordan et al. | |
| 4,865,855 A | 9/1989 | Hansen et al. | |
| 4,972,848 A | 11/1990 | DiDomenico | |
| 5,286,479 A | 2/1994 | Garlich et al. | |
| 5,356,630 A | 10/1994 | Laurencin et al. | |
| 5,721,359 A | 2/1998 | Dunn et al. | |
| 6,228,393 B1 | 5/2001 | DiCosmo et al. | |
| 6,350,738 B1 | 2/2002 | Savage et al. | |
| 6,486,148 B2 | 11/2002 | Savage et al. | |
| 6,562,318 B1 | 5/2003 | Filler | |
| 6,673,771 B1 * | 1/2004 | Greene et al. | 514/16.7 |
| 6,767,904 B2 | 7/2004 | Savage et al. | |
| 6,939,376 B2 | 9/2005 | Shulze et al. | |
| 7,282,214 B2 | 10/2007 | Wilcox et al. | |
| 7,381,439 B2 | 6/2008 | Hilgren et al. | |
| 7,598,234 B2 | 10/2009 | Savage et al. | |
| 7,659,061 B2 | 2/2010 | Hendl et al. | |
| 7,754,705 B2 | 7/2010 | Savage et al. | |
| 7,854,941 B2 | 12/2010 | Urban et al. | |
| 8,211,879 B2 | 7/2012 | Savage et al. | |
| 8,529,681 B1 | 9/2013 | Hibbs et al. | |
| 8,623,416 B2 | 1/2014 | Zasloff et al. | |
| 8,691,252 B2 | 4/2014 | Savage | |
| 8,784,857 B2 | 7/2014 | Savage | |
| 2002/0091278 A1 | 7/2002 | Savage et al. | |
| 2004/0009227 A1 | 1/2004 | Yao | |
| 2005/0032765 A1 | 2/2005 | Savage et al. | |
| 2005/0075321 A1 | 4/2005 | Ahlem et al. | |
| 2005/0244468 A1 | 11/2005 | Huang et al. | |
| 2005/0267051 A1 | 12/2005 | Lee et al. | |
| 2006/0062742 A1 | 3/2006 | Davis et al. | |
| 2006/0269485 A1 | 11/2006 | Friedman et al. | |
| 2007/0106393 A1 | 5/2007 | Miles et al. | |
| 2007/0190066 A1 | 8/2007 | Savage et al. | |
| 2007/0190067 A1 | 8/2007 | Savage et al. | |
| 2007/0190558 A1 | 8/2007 | Savage et al. | |
| 2008/0174035 A1 | 7/2008 | Winterton | |
| 2008/0188819 A1 | 8/2008 | Kloke et al. | |
| 2009/0016973 A1 | 1/2009 | Ratcliff et al. | |
| 2009/0068122 A1 | 3/2009 | Pilch et al. | |
| 2009/0324517 A1 | 12/2009 | Kline | |
| 2010/0330086 A1 | 12/2010 | Savage et al. | |
| 2011/0091376 A1 | 4/2011 | Savage | |
| 2011/0123624 A1 | 5/2011 | Zasloff | |
| 2012/0088733 A1 | 4/2012 | Kim et al. | |
| 2012/0107382 A1 | 5/2012 | Savage et al. | |
| 2013/0022651 A1 | 1/2013 | Savage | |
| 2013/0053507 A1 | 2/2013 | Savage | |
| 2013/0236619 A1 | 9/2013 | Savage | |
| 2013/0243823 A1 | 9/2013 | Genberg et al. | |
| 2013/0243840 A1 | 9/2013 | Savage et al. | |
| 2013/0245760 A1 | 9/2013 | Savage et al. | |
| 2013/0280391 A1 | 10/2013 | Savage | |
| 2014/0107090 A1 | 4/2014 | Beus et al. | |
| 2014/0194401 A1 | 7/2014 | Genberg et al. | |
| 2014/0271761 A1 | 9/2014 | Savage et al. | |
| 2014/0274913 A1 | 9/2014 | Savage et al. | |
| 2014/0315873 A1 | 10/2014 | Beus et al. | |

FOREIGN PATENT DOCUMENTS

| | | |
|---|---|---|
| CN | 102172356 | 9/2011 |
| EP | 0341951 | 11/1989 |
| WO | WO 9524415 | 9/1995 |
| WO | WO 9944616 | 9/1999 |
| WO | WO 0042058 | 7/2000 |

(Continued)

OTHER PUBLICATIONS

U.S. Appl. No. 13/783,007, filed Mar. 1, 2013, Savage.
U.S. Appl. No. 14/288,126, filed May 27, 2014, Savage et al.
U.S. Appl. No. 14/399,342, filed Jul. 23, 2014, Vazquez et al.
U.S. Appl. No. 14/341,304, filed Jul. 25, 2014, Savage et al.
U.S. Appl. No. 14/364,283, filed Jul. 29, 2014, Vazquez et al.

(Continued)

*Primary Examiner* — Snigdha Maewall
(74) *Attorney, Agent, or Firm* — Workman Nydegger

(57) ABSTRACT

Disclosed herein are methods of promoting osteogenesis in a subject, comprising administering a composition comprising a therapeutically effective amount of at least one cationic steroid antimicrobial (CSA). Also disclosed herein are methods of promoting osteogenesis in a subject in need of such promotion, comprising administering a composition comprising a therapeutically effective amount of at least one CSA. Additionally, disclosed herein are compounds and compositions comprising at least one CSA, or a pharmaceutically acceptable salt thereof, for use in the treatment of bone disease or the treatment of broken bones. Kits comprising such compositions and instructions on such methods are also contemplated herein.

37 Claims, 7 Drawing Sheets

(56) References Cited

FOREIGN PATENT DOCUMENTS

| WO | WO 0214342 | 2/2002 |
|---|---|---|
| WO | WO 03015757 | 2/2003 |
| WO | WO 03090799 | 11/2003 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | 2008-038965 | 4/2008 |
| WO | WO 2009079066 | 6/2009 |
| WO | WO 2010036427 | 4/2010 |
| WO | 2010-062562 | 6/2010 |
| WO | WO2010062562 * | 6/2010 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO2013/109236 | 7/2013 |

OTHER PUBLICATIONS

U.S. Appl. No. 14/398,094, filed Oct. 30, 2014, Savage et al.
U.S. Appl. No. 14/515,858, filed Oct. 16, 2014, Savage et al.
P. B. Savage, et al., "Thin Films Containing Ceragenins Prevent Biofilm Formation on Endotracheal Tubes", 9th International Federation of Infection Control Congress, Oct. 14, 2008, pp. 1-1.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Savage, et al., "Antibacterial Activities of Thin Films Containing Ceragenins", Microbial Surfaces: Structure, Interactions and Reactivity, ACS, May 30, 2008, pp. 65-78.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Isogai E et al: "Ceragenin CSA-13 exhibits antimicrobial activity against cariogenic and periodontopathic bacteria", Oral Microbiology and Immunology, vol. 24, No. 2, Apr. 2009, pp. 170-172.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840.
Alhanout K et al: "Squalamine as an example of a new potent antimicrobial agents class: a critical review.", Current Medicinal Chemistry 2010, vol. 17, No. 32, 2010, pp. 3909-3917.
International Search Report for PCT Application No. PCT/US2012/047750, Mailed Date: Oct. 5, 2012, Filed Date: Sep. 27, 2012, 3 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, Nov. 2002, pp. 1-7.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
Ding, et al., "Origins of cell selectivity of cationic steroid antibiotics", Journal of American Chemical Society, Oct. 2004, pp. 13642-13648.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
International Search Report for PCT Application No. PCT/US2013/038090, Mailed Date: Jul. 24, 2013.
Steeneveld, et al., "Cow-specific treatment of clinical mastitis: an economic approach", Journal of Dairy Science vol. 94, Jan. 2011, pp. 174-188.
International Search Report for PCT Application No. PCT/US2012/055248 dated Feb. 14, 2013.
International Search Report for PCT Application No. PCT/US2012/055244 dated Dec. 5, 2012.
U.S. Appl. No. 13/554,957, filed Apr. 1, 2014, Office Action.
U.S. Appl. No. 13/554,957, filed Aug. 1, 2014, Notice of Allowance.
U.S. Appl. No. 13/594,608, filed Jan. 30, 2014, Office Action.
U.S. Appl. No. 13/594,612, filed May 15, 2014, Office Action.
U.S. Appl. No. 13/615,324, filed Jan. 30, 2014, Office Action.
U.S. Appl. No. 13/554,930, filed Jul. 11, 2014, Office Action.
U.S. Appl. No. 13/783,131, filed Oct. 23, 2014, Office Action.
U.S. Appl. No. 13/000,010, filed Dec. 4, 2012, Restriction Requirement.
U.S. Appl. No. 14/056,122, filed Sep. 3, 2014, Office Action.
Qunying Guan et al. "Preparation and Characterization of Cholic Acid-Derived Antimicrobial Agents with Controlled Stabilities" Organic Letter, American Chemical Society, U.S., Co. 2, No. 18—Sep. 7, 2000.
Li Chunhong et al. "Antimicrobial activities of amine-and guanidine-functionalized cholic acid derivatives", Antimicrobial Agents and Chemotherapy, American Society for Microbiology, Washington DC, U.S., vol. 43, No. 6, Jun. 1, 1999.
Melinda Yin et al. "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1. Jan. 1, 2002.
Qunying Guan et al: "Supporting Information: Preparation and Characterization of Cholic Acid-Derived Antimicrobial Agents with Controlled Stabilities", Organic Letters, Aug. 17, 2000, pp. 1-7, XP55017313, Retrieved from the Internet: URL:http://pubs.acs.org/doi/suppl/10.1021/ol0062704/suppl file/ol0062704 sl.pdf.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999, pp. 1865-1868, XP004155984, ISSN: 0040-4039, DOI: 10.1016/S0040-4039(99)00075-1.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Fritsch et al, "In Vitro Activity of Nine Developmental Cationic Steroid Compounds (Ceragenins) against Clnical Isolates of *Clostridium difficile*", The 46th Interscience Conference on Antimicrobial Agents and Chemotherapy, Sep. 27, 2006, pp. 1-1.
International Search Report for PCT Application No. PCT/US2009/047485 dated Jan. 31, 2012.
International Search Report for PCT Application No. PCT/US2011/059225 dated Jan. 31, 2012.
U.S. Appl. No. 13/288,902, filed Nov. 3, 2011, Restriction Requirement dated Jun. 21, 2012.
U.S. Appl. No. 13/288,902, filed Nov. 3, 2011, Office Action dated Nov. 7, 2012.

(56) References Cited

OTHER PUBLICATIONS

U.S. Appl. No. 13/288,902, filed Nov. 3, 2011, Notice of Allowance dated Aug. 9, 2013.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Suzuki et al., "Molecular Genetics of Plant Sterol Backbone Synthesis", 2007; Lipids; 42: 47-54.
Van Den Bogaard et al., "Antibiotic Usage in Animals: Impact on Bacterial Resistance and Public Health"; 1999; Drugs; 58 (4): 589-607.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.

\* cited by examiner

COMPOSITIONS AND METHODS FOR TREATING BONE DISEASES AND BROKEN BONES

CROSS-REFERENCE TO RELATED APPLICATIONS

This application claims the benefit of priority to U.S. Provisional Application No. 61/534,185, filed Sep. 13, 2011, which is hereby expressly incorporated by reference in its entirety.

BACKGROUND

1. Field

Cationic steroidal antimicrobials ("CSAs") for treating certain diseases and/or promoting osteogenesis.

2. Description of the Related Art

Osteogenesis (or ossification) is the process of laying down new bone material by cells called osteoblasts. It is synonymous with bone tissue formation. There are two processes resulting in the formation of normal, healthy bone tissue: intramembranous ossification is the direct laying down of bone into the primitive connective tissue (mesenchyme); and endochondral ossification involves cartilage as a precursor. In fracture healing, endochondral osteogenesis is the most commonly occurring process, for example in fractures of long bones treated by plaster of Paris, whereas fractures treated by open reduction and stabilization by metal plate and screws may heal by intramembranous osteogenesis.

The exact mechanisms by which bone development is triggered remains unclear, but it involves growth factors and cytokines in some way. Therefore, a need exists to develop compositions and methods to enhance bone growth for the treatment of bone diseases and broken bones.

SUMMARY

Disclosed herein are methods of promoting osteogenesis in a subject, comprising administering a composition comprising a therapeutically effective amount of at least one cationic steroid antimicrobial (CSA). We have discovered that CSAs have hithertofore unappreciated activity in affecting several genes and biological pathways and mechanisms that promote bone formation and bone healing. We demonstrate new bone formation as a result of CSA administration. Also disclosed herein are methods of promoting osteogenesis in a subject in need of such promotion, comprising administering a composition comprising a therapeutically effective amount of at least one CSA. Additionally, disclosed herein are compounds and compositions comprising at least one CSA, or a pharmaceutically acceptable salt thereof, for use in the treatment of bone disease or the treatment of broken bones. Kits comprising such compositions and instructions on such methods are also contemplated herein.

Some embodiments provide for a composition, comprising at least one cationic steroid antimicrobial (CSA), or a pharmaceutically acceptable sat thereof, for use in the treatment of bone disease or treatment of a broken bone. Other embodiments provide for a method of promoting osteogenesis in a subject in need of treatment for a bone disease or healing a broken bone, comprising identifying a subject in need of treatment for a bone disease or healing a broken bone and administering at least one cationic steroid antimicrobial (CSA), or a pharmaceutically acceptable sat thereof. In some embodiments, the use of the compositions and/or methods further comprises administering at least one growth factor. In some embodiments, the use of the compositions and/or methods further comprises administering an antimicrobial agent to treat or prevent infection. In some embodiments, the CSA, or a pharmaceutically acceptable salt thereof, treats the bone disease or heals the broken bone and treats or prevent infection.

In some embodiments, the use of the compositions and/or methods comprises administering the CSA from a pharmaceutically acceptable device such as bandages, surgical dressings, gauzes, adhesive strips, surgical staples, clips, hemostats, intrauterine devices, sutures, trocars, catheters, tubes, and implants. In some embodiments, examples of implants include pills, pellets, rods, screws, wafers, discs, sponges, and tablets. In some embodiments, the sponge is an absorbable collagen sponge.

In some embodiments, the bone diseases include bone resorption, osteoarthritis, osteoporosis, osteomalacia, osteitis fibrosa cystica, osteochondritis dissecans, osteomalacia, osteomyelitis, osteoblastogenesis, osteopenia, osteonecrosis, and porotic hyperostosis. In some embodiments, the bone disease is not an infection. In some embodiments, the broken bone results from a traumatic fracture; a critical sized bone defect; distraction osteogenesis; spine fusion surgery; joint replacement; an orthopaedic implant; or a biopsy.

In some embodiments, the CSA is a compound of Formula (V) or a pharmaceutically acceptable salt thereof:

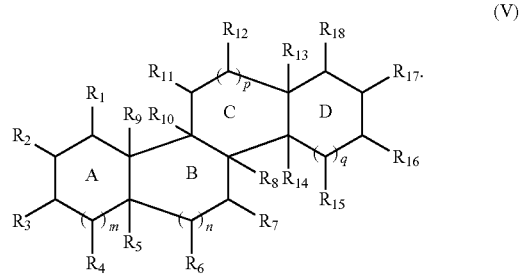

(V)

In some embodiments, the CSA, or a pharmaceutically acceptable salt thereof, is selected from the compound of Formula (I):

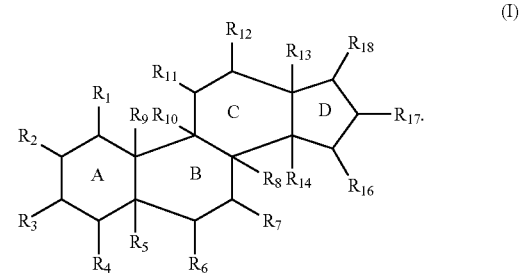

(I)

In some embodiments, the CSA, or a pharmaceutically acceptable salt thereof, is selected from the compound of Formula (Ia):

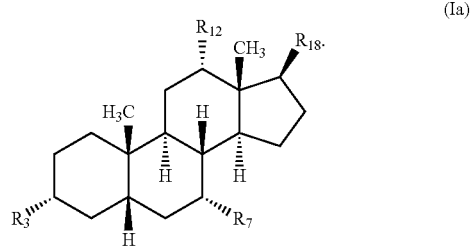

(Ia)

In some embodiments rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted alkylcarboxyalkyl, a substituted or unsubstituted alkylaminoalkyl, a substituted or unsubstituted alkylaminoalkylamino, a substituted or unsubstituted alkylaminoalkylaminoalkylamino, a substituted or unsubstituted aminoalkyl, a substituted or unsubstituted aryl, a substituted or unsubstituted arylaminoalkyl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, a substituted or unsubstituted azidoalkyloxy, a substituted or unsubstituted cyanoalkyloxy, P.G.-HN—$HC(Q_5)$-$C(O)$—$O$—, a substituted or unsubstituted guanidinoalkyloxy, a substituted or unsubstituted quaternaryammoniumalkylcarboxy, and a substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, a substituted or unsubstituted hydroxyalkyl, a substituted or unsubstituted alkyloxyalkyl, a substituted or unsubstituted aminoalkyl, a substituted or unsubstituted aryl, a substituted or unsubstituted haloalkyl, a substituted or unsubstituted alkenyl, a substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, and guanidinoalkylcarboxy, where Q5 is a side chain of any amino acid, P.G. is an amino protecting group, provided that at least two or three of $R_{1-4}$, $R_6$, $R_7$, $R_{11}$, $R_{12}$, $R_{15}$, $R_{16}$, $R_{17}$ and $R_{18}$ are independently selected from the group consisting of a substituted or unsubstituted aminoalkyl, a substituted or unsubstituted aminoalkyloxy, a substituted or unsubstituted alkylcarboxyalkyl, a substituted or unsubstituted alkylaminoalkylamino, a substituted or unsubstituted alkylaminoalkylaminoalkylamino, a substituted or unsubstituted aminoalkylcarboxy, a substituted or unsubstituted arylaminoalkyl, a substituted or unsubstituted amino alkyloxyamino alkylaminocarbonyl, a substituted or unsubstituted aminoalkylaminocarbonyl, a substituted or unsubstituted aminoalkylcarboxyamido, a quaternaryammoniumalkylcarboxy, a substituted or unsubstituted di(alkyl)aminoalkyl, a substituted or unsubstituted C-carboxyalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—HC(Q5)-C(O)—O—, a substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted $(C_1-C_{18})$ alkyl, a substituted or unsubstituted $(C_1-C_{18})$ hydroxyalkyl, a substituted or unsubstituted $(C_1-C_{18})$ alkyloxy-$(C_1-C_{18})$ alkyl, a substituted or unsubstituted $(C_1-C_{18})$ alkylcarboxy-$(C_1-C_{18})$ alkyl, a substituted or unsubstituted $(C_1-C_{18})$ alkylamino-$(C_1-C_{18})$alkyl, a substituted or unsubstituted $(C_1-C_{18})$ alkylamino-$(C_1-C_{18})$ alkylamino, a substituted or unsubstituted $(C_1-C_{18})$ alkylamino-$(C_1-C_{18})$ alkylamino-$(C_1-C_{18})$ alkylamino, a substituted or unsubstituted $(C_1-C_{18})$ aminoalkyl, a substituted or unsubstituted aryl, a substituted or unsubstituted arylamino-$(C_1-C_{18})$ alkyl, a substituted or unsubstituted $(C_1-C_{18})$ haloalkyl, a substituted or unsubstituted $C_2-C_6$ alkenyl, a substituted or unsubstituted $C_2-C_6$ alkynyl, oxo, a linking group attached to a second steroid, a substituted or unsubstituted $(C_1-C_{18})$ aminoalkyloxy, a substituted or unsubstituted $(C_1-C_{18})$ aminoalkyloxy-$(C_1-C_{18})$ alkyl, a substituted or unsubstituted $(C_1-C_{18})$ aminoalkylcarboxy, a substituted or unsubstituted $(C_1-C_{18})$ aminoalkylaminocarbonyl, a substituted or unsubstituted $(C_1-C_{18})$ aminoalkylcarboxamido, a substituted or unsubstituted di($C_1-C_{18}$ alkyl)aminoalkyl, a substituted or unsubstituted C-carboxy($C_1-C_{18}$)alkyl, $H_2N$—$HC(Q_5)$-$C(O)$—$O$—, $H_2N$—$HC(Q_5)$-$C(O)$—$N(H)$—, a substituted or unsubstituted $(C_1-C_{18})$ azidoalkyloxy, a substituted or unsubstituted $(C_1-C_{18})$ cyanoalkyloxy, P.G.-HN—$HC(Q_5)$-$C(O)$—$O$—, a substituted or unsubstituted $(C_1-C_{18})$ guanidinoalkyloxy, a substituted or unsubstituted $(C_1-C_{18})$ quaternaryammoniumalkylcarboxy, and a substituted or unsubstituted $(C_1-C_{18})$ guanidinoalkyl carboxy, where $Q_5$ is a side chain of any amino acid (including a side chain of glycine, i.e., H), and P.G. is an amino protecting group; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted $(C_1-C_{18})$ alkyl, a substituted or unsubstituted $(C_1-C_{18})$ hydroxyalkyl, a substituted or unsubstituted $(C_1-C_{18})$ alkyloxy-$(C_1-C_{18})$ alkyl, a substituted or unsubstituted $(C_1-C_{18})$ aminoalkyl, a substituted or unsubstituted aryl, a substituted or unsubstituted $(C_1-C_{18})$ haloalkyl, a substituted or unsubstituted $(C_2-C_6)$ alkenyl, a substituted or unsubstituted $(C_2-C_6)$ alkynyl, oxo, a linking group attached to a second steroid, a substituted or unsubstituted $(C_1-C_{18})$ aminoalkyloxy, a substituted or unsubstituted $(C_1-C_{18})$ aminoalkylcarboxy, a substituted or unsubstituted $(C_1-C_{18})$ aminoalkylaminocarbonyl, a substituted or unsubstituted di($C_1-C_{18}$ alkyl)aminoalkyl, a substituted or unsubstituted C-carboxy($C_1-C_{18}$)alkyl, $H_2N$—HC$(Q_5)$—$C(O)$—$O$—, $H_2N$—$HC(Q_5)$-$C(O)$—$N(H)$—, a substituted or unsubstituted $(C_1-C_{18})$ azidoalkyloxy, a substituted or unsubstituted $(C_1-C_{18})$ cyanoalkyloxy, P.G.-HN—$HC(Q_5)$—$C(O)$—$O$—, a substituted or unsubstituted $(C_1-C_{18})$ guanidinoalkyloxy, and $(C_1-C_{18})$ guanidinoalkylcarboxy, where Q5 is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1-C_{18})$ aminoalkyl, a substituted or unsubstituted $(C_1-C_{18})$ aminoalkyloxy, a substituted or unsubstituted $(C_1-C_{18})$ alkylcarboxy-$(C_1-C_{18})$ alkyl, a substituted or unsubstituted $(C_1-C_{18})$ alkylamino-$(C_1-C_{18})$ alkylamino, a substituted or unsubstituted $(C_1-C_{18})$ alkylamino-$(C_1-C_{18})$ alkylamino $(C_1-C_{18})$ alkylamino, a substituted or unsubstituted $(C_1-C_{18})$ aminoalkylcarboxy, a substituted or unsubstituted arylamino $(C_1-C_{18})$ alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted ($C_1$-$C_{18}$) quaternaryammoniumalkylcarboxy, a substituted or unsubstituted di($C_1$-$C_{18}$ alkyl)aminoalkyl, a substituted or unsubstituted C-carboxy($C_1$-$C_{18}$)alkyl, $H_2N$—HC($Q_5$)-C(O)—O—, $H_2N$—HC($Q_5$)-C(O)—N(H)—, a substituted or unsubstituted ($C_1$-$C_{18}$) azidoalkyloxy, a substituted or unsubstituted ($C_1$-$C_{18}$) cyanoalkyloxy, P.G.-HN—HC(Q5)-C(O)—O—, a substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, a substituted or unsubstituted C-carboxy($C_1$-$C_{18}$) alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, a substituted or unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, a substituted or unsubstituted C-carboxy($C_1$-$C_{18}$) alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, a substituted or unsubstituted C-carboxy($C_1$-$C_{18}$) alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$) alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) amino alkylaminocarbonyl, an unsubstituted ($C_1$-$C_5$)aminoalkylcarboxamido, an unsubstituted di($C_1$-$C_5$ alkyl)amino-($C_1$-$C_5$) alkyl, a substituted or unsubstituted C-carboxy($C_1$-$C_5$) alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)amino alkyl; C-carboxyalkyl; alkylaminoalkyl; alkyoxycarbonylalkyl; and alkylcarboxyalkyl.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_{18}$ is alkylaminoalkyl. In some embodiments, alkoxycarbonylalkyl. In some embodiments, $R_{18}$ is di(alkyl)aminoalkyl. In some embodiments, $R_{18}$ is alkylcarboxyalkyl. In some embodiments, $R_{18}$ is C-carboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; C-carboxy-$C_4$-alkyl; $C_{13}$-alkylamino-$C_5$-alkyl; $C_6$-alkoxy-carbonyl-$C_4$-alkyl; and $C_6$-alkyl-carboxy-$C_4$-alkyl.

In some embodiments, the CSA, or a pharmaceutically acceptable salt thereof, is:

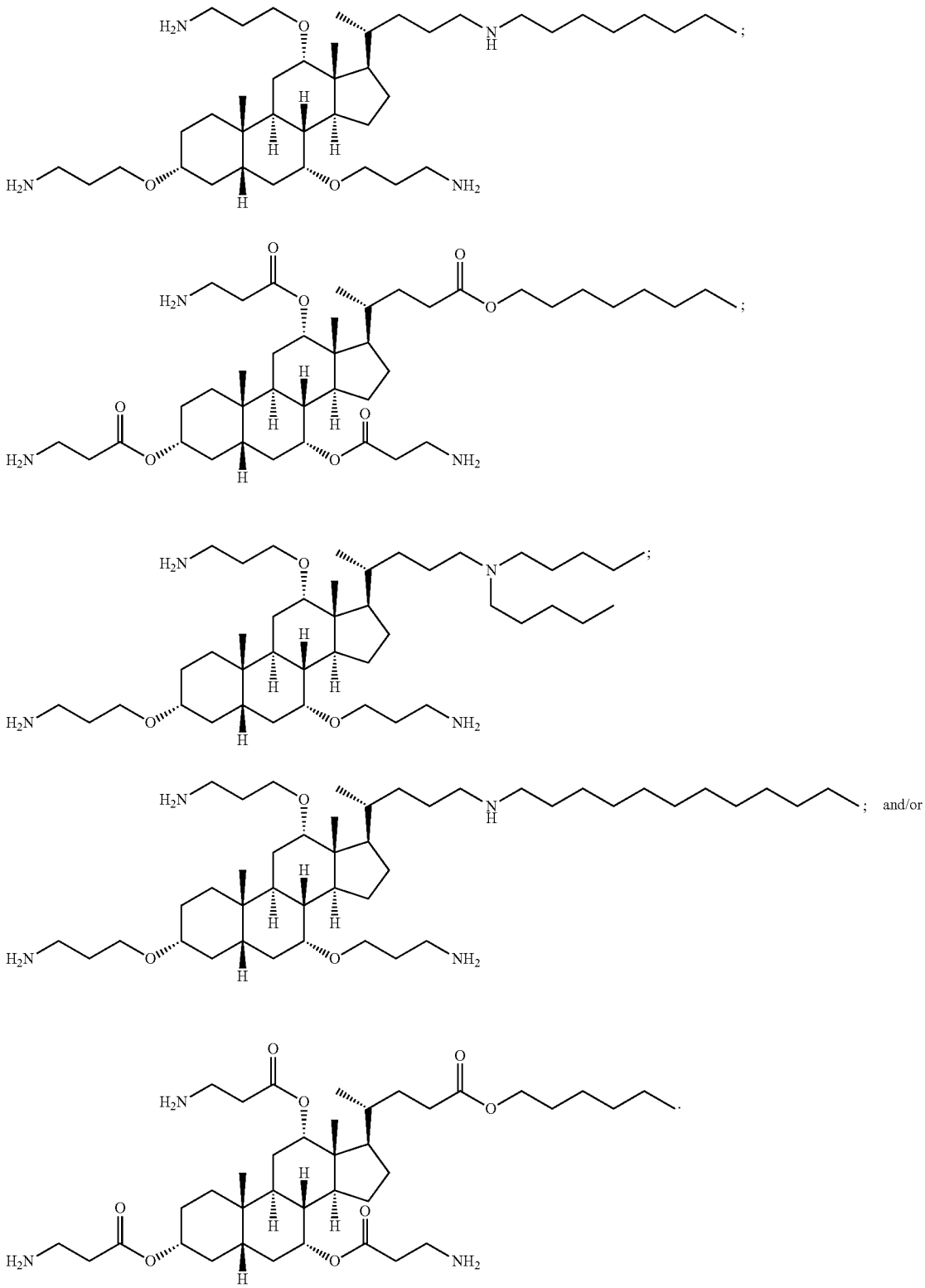

In some embodiments, the CSA, or a pharmaceutically acceptable salt thereof, is

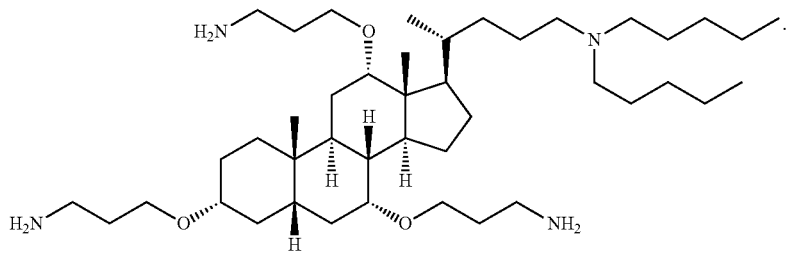

In some embodiments, the pharmaceutically acceptable salt is a hydrochloride salt. In some embodiments, the pharmaceutically acceptable salt is a tri-hydrochloride salt.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

DETAILED DESCRIPTION

Figure 1:
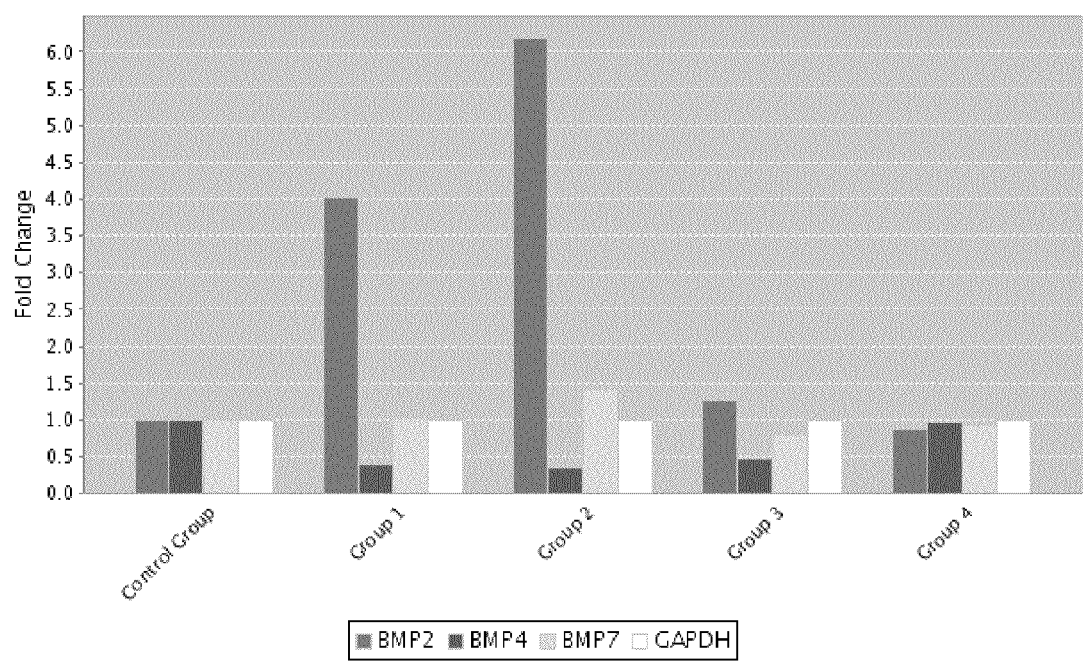
FIG. 1: BMP up-regulation in hMSC cells treated with CSA after 8 hours dosing.

The embodiments disclosed herein will now be described by reference to some more detailed embodiments, with occasional reference to the accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Definitions

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$, $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO(CH_2)_mO—$, $R^b(CH_2)_nO—$, $R^cC(O)O(CH_2)_pO—$, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3—$, $CH_3CH_2—$, $CH_3CH_2CH_2—$, $(CH_3)_2CH—$, $CH_3CH_2CH_2CH_2—$, $CH_3CH_2CH(CH_3)—$ and $(CH_3)_3C—$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxyalkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N$_3$ group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "C-carboxyalkyl" refers to a carboxy group connected, as a substituent, to an alkyl group. Examples include HO—(C=O)-alkyl, with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

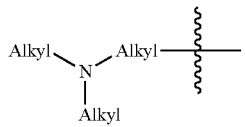

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "azidoalkyloxy" refers to an azido group connected as a substituent, to an alkyloxy group. Examples include N$_3$-alkyl-O— and N$_3$-alkoxy- with the terms alkyl and alkoxy as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

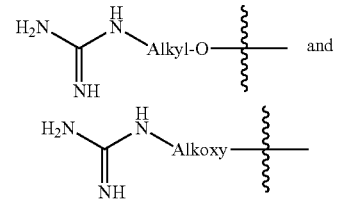

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

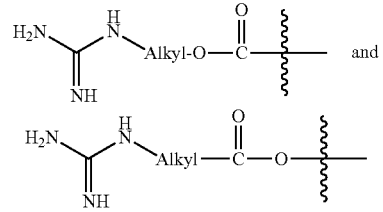

with the term alkyl as defined herein.

As used herein, "quaternaryammoniumalkylcarboxy" refers to a quaternized amino group connected, as a substituent, to an alkyl group connected, as a substituent, to a carboxy group. Examples include

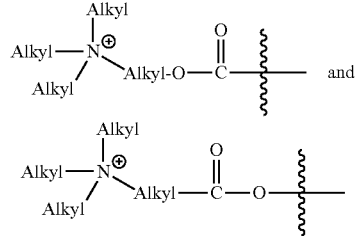

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is $(C_1-C_{10})$ alkyloxy-$(C_1-C_{10})$ alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Compounds and Compositions

Compounds useful in accordance with this disclosure are described herein, both generically and with particularity, and in U.S. Pat. Nos. 6,350,738, 6,486,148, 6,767,904, 7,598,234, and 7,754,705, which are incorporated herein by reference. Compounds include steroid derivatives, such as cationic steroid antimicrobials ("CSAs") that exhibit one or more osteogenesis activities or functions. The skilled artisan will recognize the compounds within the generic formula set forth herein. Additional compounds of the disclosure having one or more osteogenesis activities or functions are described and can be characterized using the assays set forth herein and in the art.

Some embodiments disclosed herein relate to a compound selected from Formula (V) or a pharmaceutically acceptable salt of the foregoing and can have the structure:

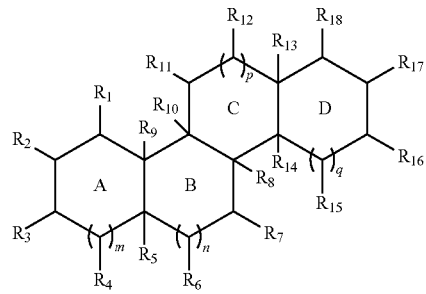

(V)

wherein rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN-HC$(Q_5)$-C(O)-O-, substituted or unsubstituted guanidinoalkyloxy, substituted or unsubstituted quaternaryammoniumalkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N$—$HC(Q_5)$-C(O)—O—, $H_2N$—$HC(Q_5)$-C(O)—N(H)—, substituted or unsubstituted azidoalkyloxy, substituted or unsubstituted cyanoalkyloxy, P.G.-HN—$HC(Q_5)$-C(O)—O—, substituted or unsubstituted guanidinoalkyloxy, and substituted or unsubstituted guanidinoalkylcarboxy, where Q5 is a side chain of any amino acid, P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a substituted or unsubstituted quaternaryammoniumalkylcarboxy, a substituted or unsubstituted di(alkyl)aminoalkyl, a substituted or unsubstituted C-carboxyalkyl, $H_2N$—$HC(Q_5)$-C(O)—O—, $H_2N$—HC$(Q_5)$-C(O)—N(H)—, substituted or unsubstituted azidoalkyloxy, substituted or unsubstituted cyanoalkyloxy, P. G.-HN—HC(Q5)-C(O)—O—, substituted or unsubstituted guanidinoalkyloxy, and a substituted or unsubstituted guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$)alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, a substituted or unsubstituted ($C_1$-$C_{18}$) aminoalkyl, a substituted or unsubstituted aryl, a substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, a substituted or unsubstituted ($C_1$-$C_{18}$)aminoalkylcarboxy, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted di($C_1$-$C_{18}$ alkyl)aminoalkyl, a substituted or unsubstituted C-carboxy($C_1$-$C_{18}$)alkyl, $H_2N$—$HC(Q_5)$-C(O)—O—, $H_2N$—$HC(Q_5)$-C(O)—N(H)—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-C(O)—O—, substituted or unsubstituted ($C_1$-$C_{18}$) guanidinoalkyloxy, substituted or unsubstituted ($C_1$-$C_{18}$) quaternaryammoniumalkylcarboxy, and substituted or unsubstituted ($C_1$-$C_{18}$) guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, di($C_1$-$C_{18}$ alkyl)aminoalkyl, a substituted or unsubstituted C-carboxy($C_1$-$C_{18}$)alkyl, $H_2N$—$HC(Q_5)$-C(O)—O—, $H_2N$—$HC(Q_5)$-C(O)—N(H)—, substituted or unsubstituted ($C_1$-$C_{18}$) azidoalkyloxy, substituted or unsubstituted ($C_1$-$C_{18}$) cyanoalkyloxy, P. G.-HN—$HC(Q_5)$-C(O)—O—, substituted or unsubstituted ($C_1$-$C_{18}$) guanidinoalkyloxy, and substituted or unsubstituted ($C_1$-$C_{18}$) guanidinoalkylcarboxy, where Q5 is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxyamido, a substituted or unsubstituted ($C_1$-$C_{18}$) quaternaryammoniumalkylcarboxy, substituted or unsubstituted di($C_1$-$C_{18}$ alkyl)aminoalkyl, a substituted or unsubstituted C-carboxy($C_1$-$C_{18}$)alkyl, $H_2N$—$HC(Q_5)$—C(O)—O—, $H_2N$—$HC(Q_5)$-C(O)—N(H)—, substituted or unsubstituted ($C_1$-$C_{18}$) azidoalkyloxy, substituted or unsubstituted ($C_1$-$C_{18}$) cyanoalkyoxy, P.G.-HN—HC(Q5)-C(O)—O—, substituted or unsubstituted ($C_1$-$C_{18}$) guanidinoalkyloxy, and a substituted or unsubstituted ($C_1$-$C_{18}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{10}$ aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted C-carboxy ($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$)

alkylamino-$(C_1-C_{18})$ alkylamino, an unsubstituted $(C_1-C_{18})$ aminoalkyl, an unsubstituted aryl, an unsubstituted arylamino-$(C_1-C_{18})$ alkyl, oxo, an unsubstituted $(C_1-C_{18})$ aminoalkyloxy, an unsubstituted $(C_1-C_{18})$ aminoalkyloxy-$(C_1-C_{18})$ alkyl, an unsubstituted $(C_1-C_{18})$ aminoalkylcarboxy, an unsubstituted $(C_1-C_{18})$ aminoalkylaminocarbonyl, an unsubstituted $(C_1-C_{18})$ aminoalkylcarboxamido, an unsubstituted di$(C_1-C_{18}$ alkyl)aminoalkyl, unsubstituted C-carboxy$(C_1-C_{18})$alkyl, unsubstituted $(C_1-C_{18})$ guanidinoalkyloxy, unsubstituted $(C_1-C_{18})$ quaternaryammoniumalkylcarboxy, and unsubstituted $(C_1-C_{18})$ guanidinoalkyl carboxy; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted $(C_1-C_{18})$ alkyl, unsubstituted $(C_1-C_{18})$ hydroxyalkyl, unsubstituted $(C_1-C_{18})$ alkyloxy-$(C_1-C_{18})$ alkyl, unsubstituted $(C_1-C_{18})$ alkylcarboxy-$(C_1-C_{18})$ alkyl, unsubstituted $(C_1-C_{18})$ alkylamino-$(C_1-C_{18})$ alkyl, unsubstituted $(C_1-C_{18})$ alkylamino-$(C_1-C_{18})$ alkylamino, unsubstituted $(C_1-C_{18})$ alkylamino-$(C_1-C_{18})$ alkylamino-$(C_1-C_{18})$ alkylamino, an unsubstituted $(C_1-C_{18})$ aminoalkyl, an unsubstituted aryl, an unsubstituted arylamino-$(C_1-C_{18})$ alkyl, oxo, an unsubstituted $(C_1-C_{18})$ aminoalkyloxy, an unsubstituted $(C_1-C_{18})$ aminoalkyloxy-$(C_1-C_{18})$ alkyl, an unsubstituted $(C_1-C_{18})$ aminoalkylcarboxy, an unsubstituted $(C_1-C_{18})$ aminoalkylaminocarbonyl, an unsubstituted $(C_1-C_{18})$ aminoalkylcarboxamido, an unsubstituted di$(C_1-C_{18}$ alkyl)aminoalkyl, unsubstituted C-carboxy$(C_1-C_{18})$alkyl, unsubstituted $(C_1-C_{18})$ guanidinoalkyloxy, unsubstituted $(C_1-C_{18})$ quaternaryammoniumalkylcarboxy, and unsubstituted $(C_1-C_{18})$ guanidino alkyl carboxy.

In some embodiments, the compounds or pharmaceutically acceptable salts thereof of Formula (V) can be also represented by Formula (I):

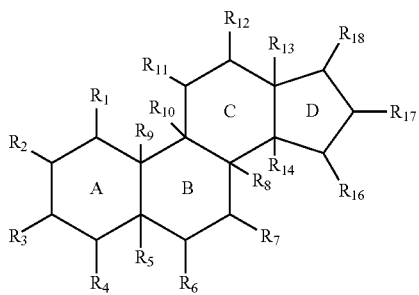

(I)

where substituents are as defined herein.

In some embodiments, rings A, B, C, and D are independently saturated.

In some embodiments, one or more of rings A, B, C, and D are heterocyclic.

In some embodiments, rings A, B, C, and D are non-heterocyclic.

In some embodiments, $R_3$, $R_7$, $R_{12}$, and $R_{18}$ are independently selected from the group consisting of hydrogen, an unsubstituted $(C_1-C_{18})$ alkyl, unsubstituted $(C_1-C_{18})$ hydroxyalkyl, unsubstituted $(C_1-C_{18})$ alkyloxy-$(C_1-C_{18})$ alkyl, unsubstituted $(C_1-C_{18})$ alkylcarboxy-$(C_1-C_{18})$ alkyl, unsubstituted $(C_1-C_{18})$ alkylamino-$(C_1-C_{18})$alkyl, unsubstituted $(C_1-C_{18})$ alkylamino-$(C_1-C_{18})$ alkylamino, unsubstituted $(C_1-C_{18})$ alkylamino-$(C_1-C_{18})$ alkylamino-$(C_1-C_{18})$ alkylamino, an unsubstituted $(C_1-C_{18})$ aminoalkyl, an unsubstituted arylamino-$(C_1-C_{18})$ alkyl, an unsubstituted $(C_1-C_{18})$ aminoalkyloxy, an unsubstituted $(C_1-C_{18})$ amino alkyloxy-$(C_1-C_{18})$ alkyl, an unsubstituted $(C_1-C_{18})$ aminoalkylcarboxy, an unsubstituted $(C_1-C_{18})$ aminoalkylaminocarbonyl, an unsubstituted $(C_1-C_{18})$ aminoalkylcarboxamido, an unsubstituted di$(C_1-C_{18}$ alkyl)aminoalkyl, unsubstituted C-carboxy$(C_1-C_{18})$alkyl, unsubstituted $(C_1-C_{18})$ guanidinoalkyloxy, unsubstituted $(C_1-C_{18})$ quaternaryammoniumalkylcarboxy, and unsubstituted $(C_1-C_{18})$ guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In some embodiments, $R_3$, $R_7$, $R_{12}$, and $R_{18}$ are independently selected from the group consisting of hydrogen, an unsubstituted $(C_1-C_6)$ alkyl, unsubstituted $(C_1-C_6)$ hydroxyalkyl, unsubstituted $(C_1-C_{16})$ alkyloxy-$(C_1-C_5)$ alkyl, unsubstituted $(C_1-C_{16})$ alkylcarboxy-$(C_1-C_5)$ alkyl, unsubstituted $(C_1-C_{16})$ alkylamino-$(C_1-C_5)$alkyl, unsubstituted $(C_1-C_{16})$ alkylamino-$(C_1-C_5)$ alkylamino, unsubstituted $(C_1-C_{16})$ alkylamino-$(C_1-C_{16})$ alkylamino-$(C_1-C_5)$ alkylamino, an unsubstituted $(C_1-C_{16})$ aminoalkyl, an unsubstituted arylamino-$(C_1-C_5)$ alkyl, an unsubstituted $(C_1-C_5)$ aminoalkyloxy, an unsubstituted $(C_1-C_{16})$ aminoalkyloxy-$(C_1-C_5)$ alkyl, an unsubstituted $(C_1-C_5)$ aminoalkylcarboxy, an unsubstituted $(C_1-C_5)$ aminoalkylaminocarbonyl, an unsubstituted $(C_1-C_5)$aminoalkylcarboxamido, an unsubstituted di$(C_1-C_5$ alkyl)amino-$(C_1-C_5)$ alkyl, unsubstituted C-carboxy$(C_1-C_5)$alkyl, unsubstituted $(C_1-C_5)$ guanidinoalkyloxy, unsubstituted $(C_1-C_{16})$ quaternaryammoniumalkylcarboxy, and unsubstituted $(C_1-C_{16})$ guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; C-carboxyalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)amino alkyl; C-carboxyalkyl; alkylaminoalkyl; alkyoxycarbonylalkyl; and alkylcarboxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_3$, $R_7$, and $R_{12}$ are aminoalkylcarboxy.

In some embodiments, $R_{18}$ is alkylaminoalkyl.

In some embodiments, $R_{18}$ is alkoxycarbonylalkyl.

In some embodiments, $R_{18}$ is di(alkyl)aminoalkyl.

In some embodiments, $R_{18}$ is alkylcarboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-$(C_5$-alkyl)amino-$C_5$-alkyl; C-carboxy-$C_4$-alkyl; $C_{13}$-alkylamino-$C_5$-alkyl; $C_6$-alkoxy-carbonyl-$C_4$-alkyl; and $C_6$-alkyl-carboxy-$C_4$-alkyl.

In some embodiments, the compounds or pharmaceutically acceptable salts thereof of Formula (V) can be also represented by Formula (Ia):

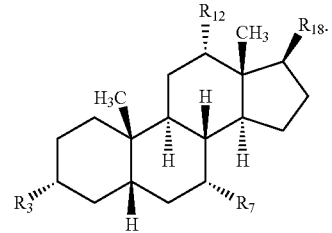

In some embodiments, the compounds or pharmaceutically acceptable salts thereof of Formula (Ia) are selected from the group consisting of:

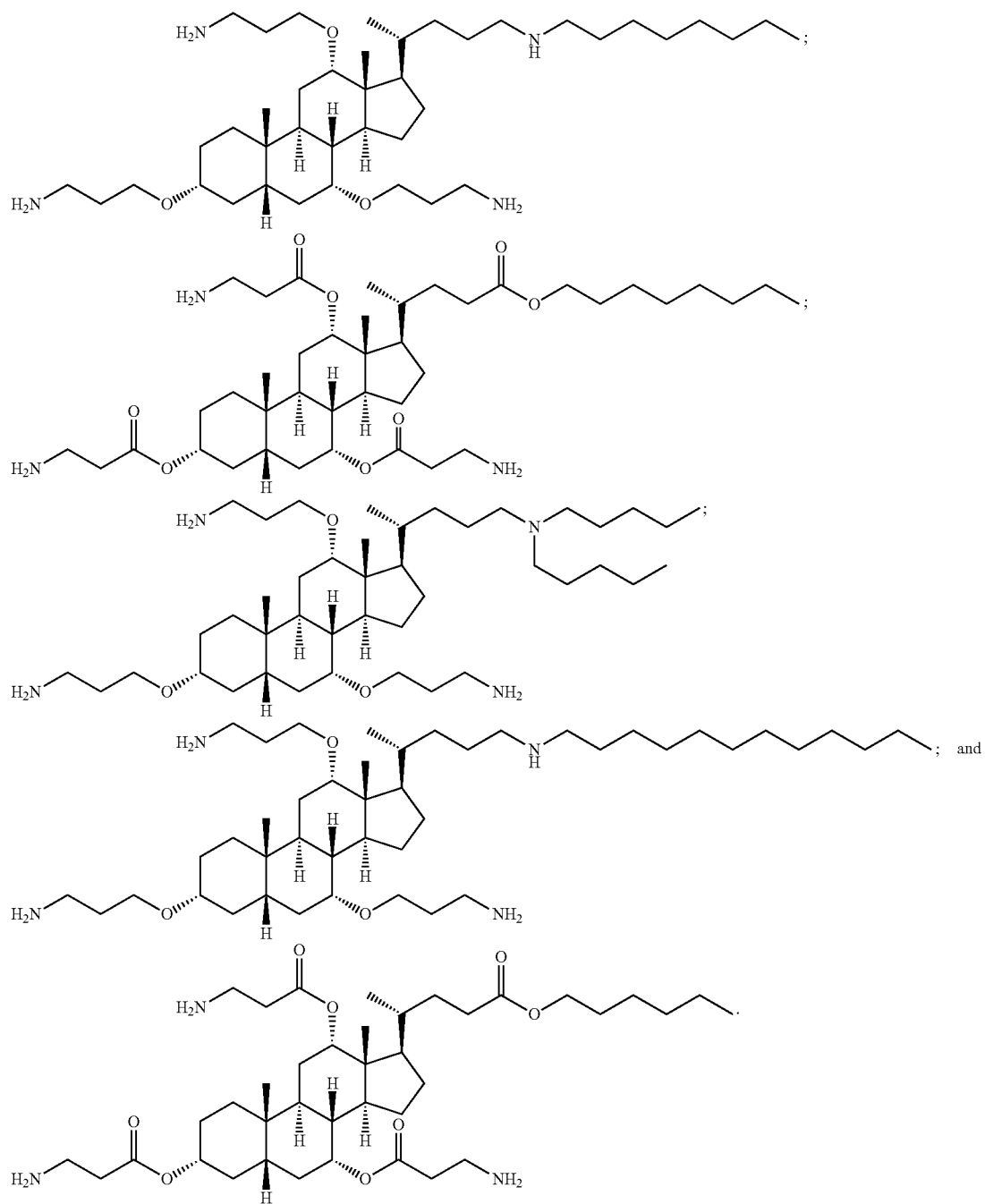
In some embodiments, the compounds or pharmaceutically acceptable salts thereof of Formula (Ia) is
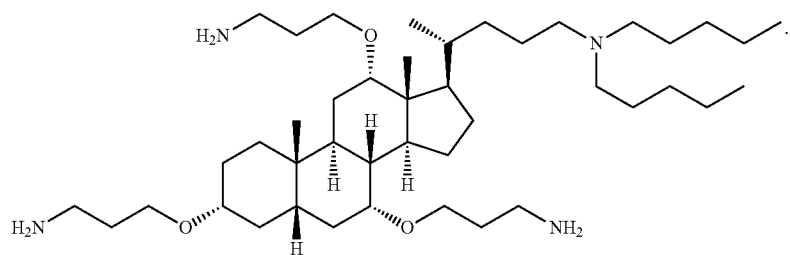

In some embodiments, the pharmaceutically acceptable salt is a hydrochloride salt.

In some embodiments, the pharmaceutically acceptable salt is a tri-hydrochloride salt.

In some embodiments, the compounds of Formula (I) are represented as follows:

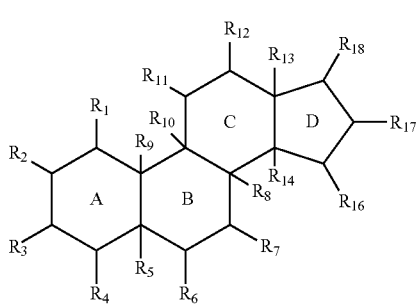

(I)

wherein fused rings A, B, C, and D are independently saturated or fully or partially unsaturated; and each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted $(C_1$-$C_{10})$ alkyl, $(C_1$-$C_{10})$ hydroxyalkyl, $(C_1$-$C_{10})$ alkyloxy-$(C_1$-$C_{10})$ alkyl, $(C_1$-$C_{10})$ alkylcarboxy-$(C_1$-$C_{10})$ alkyl, $C_1$-$C_{10})$ alkylamino-$(C_1$-$C_{10})$ alkyl, $(C_1$-$C_{10})$ alkylamino-$(C_1$-$C_{10})$ alkylamino, $(C_1$-$C_{10})$ alkylamino-$(C_1$-$C_{10})$ alkylamino-$(C_1$-$C_{10})$ alkylamino, a substituted or unsubstituted $(C_1$-$C_{10})$ aminoalkyl, a substituted or unsubstituted aryl, a substituted or unsubstituted arylamino-$(C_1$-$C_{10})$ alkyl, $(C_1$-$C_{10})$ haloalkyl, $C_2$-$C_6$ alkenyl, $C_2$-$C_6$ alkynyl, oxo, a linking group attached to a second steroid, a substituted or unsubstituted $(C_1$-$C_{10})$ aminoalkyloxy, a substituted or unsubstituted $(C_1$-$C_{10})$ aminoalkyloxy-$(C_1$-$C_{10})$ alkyl, a substituted or unsubstituted $(C_1$-$C_{10})$ aminoalkylcarboxy, a substituted or unsubstituted $(C_1$-$C_{10})$ aminoalkylaminocarbonyl, a substituted or unsubstituted $(C_1$-$C_{10})$ aminoalkylcarboxamido, $H_2N$—Hc(Q5)-C(O)—O—, $H_2N$—HC(Q5)-C(O)—N(H)—, $(C_1$-$C_{10})$ azidoalkyloxy, $(C_1$-$C_{10})$ cyanoalkyloxy, P.G.-HN—HC(Q5)-C(O)—O—, $(C_1$-$C_{10})$ guanidinoalkyloxy, $(C_1$-$C_{10})$ quaternaryammoniumalkylcarboxy, and $(C_1$-$C_{10})$ guanidinoalkyl carboxy, where Q5 is a side chain of any amino acid (including the side chain of glycine, i.e., H), PG. is an amino protecting group, and $R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, 10 a substituted or unsubstituted $(C_1$-$C_{10})$ alkyl, $(C_1$-$C_{10})$ hydroxyalkyl, $(C_1$-$C_{10})$ alkyloxy-$(C_1$-$C_{10})$ alkyl, a substituted or unsubstituted $(C_1$-$C_{10})$ aminoalkyl, a substituted or unsubstituted aryl, $C_1$-$C_{10}$ haloalkyl, $C_2$-$C_6$ alkenyl, $C_2$-$C_6$ alkynyl, oxo, a linking group attached to a second steroid, a substituted or unsubstituted $(C_1$-$C_{10})$ aminoalkyloxy, a substituted or unsubstituted $(C_1$-$C_{10})$ aminoalkylcarboxy, a substituted or unsubstituted $(C_1$-$C_{10})$ aminoalkylaminocarbonyl, $H_2N$—HC(Q5)-C(O)—O—, $H_2N$—HC(Q5)-C(O)—N(H)—, $(C_1$-$C_{10})$ azidoalkyloxy, $(C_1$-$C_{10})$ cyanoalkyloxy, P.G.-HN—HC(Q5)-C(O)—O—, $(C_1$-$C_{10})$ guanidinoalkyloxy, and $(C_1$-$C_{10})$ guanidinoalkylcarboxy, where Q5 is a side chain of any amino acid, PG. is an amino protecting group, and provided that at least two of $R_1$ through $R_{14}$ are independently selected from the group consisting of a substituted or unsubstituted $(C_1$-$C_{10})$ aminoalkyloxy, $(C_1$-$C_{10})$ alkylcarboxy-$(C_1$-$C_{10})$ alkyl, $(C_1$-$C_{10})$ alkylamino-$(C_1$-$C_{10})$ alkylamino, $(C_1$-$C_{10})$ alkylamino-$(C_1$-$C_{10})$ alkylamino-$(C_1$-$C_{10})$ alkylamino, a substituted or unsubstituted $(C_1$-$C_{10})$ aminoalkylcarboxy, a substituted or unsubstituted arylamino $(C_1$-$C_{10})$ alkyl, a substituted or unsubstituted $(C_1$-$C_{10})$ aminoalkyloxy-$(C_1$-$C_{10})$ alkyl, a substituted or unsubstituted $(C_1$-$C_{10})$ aminoalkylaminocarbonyl, $(C_1$-$C_{10})$ quaternary ammonium alkylcarboxy, $H_2N$—HC(Q5)C(O)—O—, $H_2N$—HC(Q5)-C(O)—N(H)—, $(C_1$-$C_{10})$ azidoalkyloxy, $(C_1$-$C_{10})$ cyanoalkyloxy, P.G.-HN—HC(Q5)-C(O)—O—, $(C_1$-$C_{10})$ guanidinoalkyloxy, and $(C_1$-$C_{10})$ guanidinoalkylcarboxy; or a pharmaceutically acceptable salt thereof.

In some embodiments, compounds comprise a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group. The compound can also contain a hydrophobic group, such as a substituted $(C_3$-$C_{10})$ aminoalkyl group, a $(C_1$-$C_{10})$ alkyloxy $(C_3$-$C_{10})$ alkyl group, or a $(C_1$-$C_{10})$ alkylamino $(C_3$-$C_{10})$ alkyl group, attached to the steroid backbone. For example, the compound may have the Formula (V), where each of the three chains containing nitrogen-containing groups is independently selected from $R_1$ through $R_4$, $R_6$, $R_7$, $R_{11}$, $R_{12}$, $R_{15}$, $R_{16}$, $R_{17}$, and $R_{18}$, where: each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted $(C_1$-$C_{10})$ alkyl, $(C_1$-$C_{10})$ hydroxyalkyl, $(C_1$-$C_{10})$ alkyloxy-$(C_1$-$C_{10})$ alkyl, $(C_1$-$C_{10})$alkylcarboxy-$(C_1$-$C_{10})$ alkyl, $(C_1$-$C_{10})$ alkylamino-$(C_1$-$C_{10})$ alkyl, $(C_1$-$C_{10})$ alkylamino-$(C_1$-$C_{10})$ alkylamino, $(C_1$-$C_{10}$ alkylamino-$(C_1$-$C_{10})$ alkylamino-$(C_1$-$C_{10})$ alkylamino, a substituted or unsubstituted $(C_1$-$C_{10})$ aminoalkyl, a substituted or unsubstituted aryl, a substituted or unsubstituted arylamino-$(C_1$-$C_{10})$ alkyl, $(C_1$-$C_{10})$ haloalkyl, $C_2$-$C_6$ alkenyl, $C_2$-$C_6$ alkynyl, oxo, a linking group attached to a second steroid, a substituted or unsubstituted $(C_1$-$C_{10})$ aminoalkyloxy, a substituted or unsubstituted $(C_1$-$C_{10})$ aminoalkyloxy-$(C_1$-$C_{10})$ alkyl, a substituted or unsubstituted $(C_1$-$C_{10})$ aminoalkylcarboxy, a substituted or unsubstituted $(C_1$-$C_{10})$ aminoalkylaminocarbonyl, a substituted or unsubstituted $(C_1$-$C_{10})$ aminoalkylcarboxamido, $H_2N$—HC(Q5)-C(O)—O—, $H_2N$—Hc(Q5)-C(O)—N(H)—, $(C_1$-$C_{10})$ azidoalkyloxy, $(C_1$-$C_{10})$ cyanoalkyloxy, P.G.-HN—HC(Q5)-C(O)—O—, $(C_1$-$C_{10})$ guanidinoalkyloxy, $(C_1$-$C_{10})$ quaternaryammoniumalkylcarboxy, and $(C_1$-$C_{10})$ guanidino alkyl carboxy, where Q5 is a side chain of any amino acid (including a side chain of glycine, i.e., H). PG. is an amino protecting group: and each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, a substituted or unsubstituted $(C_1$-$C_{10})$ alkyl, $(C_1$-$C_{10})$ hydroxyalkyl, $(C_1$-$C_{10})$ alkyloxy-$(C_1$-$C_{10})$ alkyl, a substituted or unsubstituted $(C_1$-$C_{10})$ aminoalkyl, a substituted or unsubstituted aryl, $C_1$-$C_{10}$ haloalkyl, $C_2$-$C_6$ alkenyl, $C_2$-$C_6$ alkynyl, oxo, a linking group attached to a second steroid, a substituted or unsubstituted $(C_1$-$C_{10})$ aminoalkyloxy, a substituted or unsubstituted $(C_1$-$C_{10})$ aminoalkylcarboxy, a substituted or unsubstituted $(C_1$-$C_{10})$ aminoalkylaminocarbonyl, $H_2N$—HC(Q5)-C(O)—O—, $H_2N$—HC(Q5)-C(O)—N(H)—, $(C_1$-$C_{10})$ azidoalkyloxy, $(C_1$-$C_{10})$ cyanoalkyloxy, P.G.-HN—HC(Q5)-C(O)—O—, $(C_1$-$C_{10})$ guanidinoalkyloxy, and (—) guanidinoalkylcarboxy, where Q5 is a side chain of any amino acid, PG. is an amino protecting group, provided that at least three of $R_1$ through $R_4$, $R_6$, $R_7$, $R_{11}$, $R_{12}$, $R_{15}$, $R_{16}$, $R_{17}$, and $R_{18}$ are disposed on the same face of the ring system and are independently selected from the group consisting of a substituted or unsubstituted $(C_1-C_{10})$ aminoalkyl, a substituted or unsubstituted $(C_1-C_{10})$ aminoalkyloxy, $(C_1-C_{10})$ alkylcarboxy-$(C_1-C_{10})$ alkyl, $(C_1-C_{10})$ alkylamino-$(C_1-C_{10})$ alkylamino, $(C_1-C_{10})$ alkylamino-$(C_1-C_{10})$ alkylamino-$(C_1-C_{10})$ alkylamino, a substituted or unsubstituted $(C_1-C_{10})$ aminoalkylcarboxy, a substituted or unsubstituted arylamino-$(C_1-C_{10})$ alkyl, a substituted or unsubstituted $(C_1-C_{10})$ aminoalkyloxy-$(C_1-C_{10})$ aminoalkylaminocarbonyl, a substituted or unsubstituted $(C_1-C_{10})$ aminoalkylaminocarbonyl, a substituted or unsubstituted $(C_1-C_5)$ aminoalkylcarboxamido, a $(C_1-C_{10})$ quaternaryammoniumalkylcarboxy, $H_2N-HC(Q5)-C(O)-O-$, $H_2N-HC(Q5)C(O)-N(H)-$, $(C_1-C_{10})$ azidoalkyloxy, $(C_1-C_{10})$ cyanoalkylox, P.G.-HN-HC(Q5)-C(O)-O-$, $(C_1-C_{10})$ guanidinoalkyloxy, and a $(C_1-C_{10})$ guanidinoalkylcarboxy; or a pharmaceutically acceptable salt thereof. In various aspects, at least two, or at least, three, of m, n, p, and q are 1.

In some embodiments, the compounds set forth herein preserve certain stereochemical and electronic characteristics found in steroids. The term "same configuration" as used herein refers to substituents on the fused steroid having the same stereochemical orientation. For example, in some embodiments, substituents $R_3$, $R_7$ and $R_{12}$ are all β-substituted or α-substituted.

In some embodiments, compounds include, but are not limited to, compounds having amine or guanidine groups covalently attached to a steroid backbone or scaffold at any carbon position, e.g., cholic acid. In various embodiments, a group is covalently attached at anyone, or more, of positions C3, C7 and C12 of the steroid backbone or scaffold. In additional embodiments, a group is absent from anyone, or more, of positions C3, C7 and C12 of the steroid backbone or scaffold. Compounds that include such groups can include a tether, the tether having variable chain length or size. As used herein, the terms "tether" or "tethered," when used in reference to a compound, refers to the chain of atoms between the steroid backbone or scaffold and a terminal amino or guanidine group. In various embodiments, a tether is covalently attached at anyone, or more, of positions C3, C7 and C12. In additional embodiments, a tether is lacking at anyone, or more, of positions C3, C7 and C12. A tether length may include the heteroatom (O or N) covalently attached to the steroid backbone.

In some embodiments, other ring systems can also be used, e.g., 5-member fused rings. Compounds with backbones having a combination of 5- and 6-membered rings are also contemplated. Amine or guanidine groups can be separated from the backbone by at least one, two, three, four or more atoms. The backbone can be used to orient the amine or guanidine groups on one face, or plane, of the steroid. For example, a scheme showing a compound having primary amino groups on one face, or plane, of a backbone is shown below:

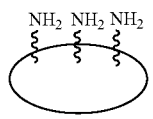

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1-C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

Pharmaceutical Compositions

While it is possible for the compounds described herein to be administered alone, it may be preferable to formulate the compounds as pharmaceutical compositions. As such, in yet another aspect, pharmaceutical compositions useful in the methods and uses of the disclosed embodiments are provided. More particularly, the pharmaceutical compositions described herein may be useful, inter alia, for treating or preventing a bone disease and/or a broken bone. A pharmaceutical composition is any composition that may be administered in vitro or in vivo or both to a subject in order to treat or ameliorate a condition. In some embodiments, the pharmaceutical composition is for veterinary use. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans. In some embodiments, the subject is a vertebrate. In other embodiments, the subject is a non-human animal As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprises a therapeutically or prophylactically effective amount of a compound described herein, together with at least one pharmaceutically acceptable excipient selected from the group consisting of—medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA comprises a multimer (e.g., a dimer, trimer, tetramer, or higher order polymer). In some exemplary embodiments, the CSAs can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition contains a total amount of the active ingredient(s) sufficient to achieve an intended therapeutic effect.

Methods and Uses

Disclosed herein are compositions comprising at least one cationic steroid antimicrobial (CSA), or a pharmaceutically acceptable sat thereof, for use in the treatment of bone disease or treatment of a broken bone. Some embodiments are methods of promoting osteogenesis in a subject in need of treatment for a bone disease or healing a broken bone, comprising identifying a subject in need of treatment for a bone disease or healing a broken bone and administering a CSA or a pharmaceutically acceptable salt thereof. In some embodiments, the bone disease is not an infection or associated with an infection.

In some embodiments, the compositions or methods further comprise administering at least one growth factor. The growth factor administered may be a bone growth factor, which may enhance osteogenesis in the subject. In some embodiments, the bone growth factor is recombinant bone morphogenetic protein. In some embodiments, the recombinant bone morphogenetic protein is recombinant human bone morphogenetic protein. In some embodiments, the bone morphogenetic protein is BMP-2. In other embodiments the bone morphogenetic protein is BMP-2, BMP-3, BMP-4, BMP-5, BMP-6, BMP-7, and/or a combination of any of the aforementioned BMPs. In some embodiments, the bone growth factor is INFUSE® BMP-2 and/or OP-1 BMP-7. The interaction between the bone growth factor and CSA may be a synergistic interaction resulting in osteogenesis at levels higher than expected from individual treatment using only a CSA or only a growth factor. In some embodiments, the interaction between the bone growth factor and CSA allows for the use of lower amounts of BMP-2 or rhBMP-2. In other embodiments, the use of CSA in combination with growth factors, including BMP-2 or rhBMP-2, reduces adverse consequences of the growth factor, including unintended growth. In some exemplary embodiments, the method further comprises administering an osteogenic nutrient, osteogenic supplement, or combinations thereof.

In some embodiments, the CSA is administered to treat a bone disease. Examples of bone diseases include bone resorption, osteoarthritis, osteoporosis, osteomalacia, osteitis fibrosa cystica, osteochondritis dissecans, osteoblastogenesis, osteomalacia, osteomyelitis, osteopenia, osteonecrosis, and porotic hyperostosis. In some embodiments, the bone disease is not an infection and/or associated with an infection.

In some embodiments, the CSA is administered to treat a broken bone. Examples of broken bones include fractures (including traumatic fractures, stress fractures, and fractures characterized by partial breakages such as greenstick fractures); critical sized bone defects; distraction osteogenesis; surgical bone alterations (including spine fusion surgery); and bone disruption resulting from a joint replacement, an orthopaedic implant, or a biopsy. One additional use is in the treatment of non-healing bone conditions, such as fractures or surgical removal or grafting of bones. While the CSAs disclosed herein can be used as an initial treatment for surgical procedures impacting bones or broken bones, existing conditions in which such bones are recalcitrant to healing can be addressed with the methods and materials disclosed herein.

The compositions disclosed herein can be administered to any bone, anywhere it is desirable to promote bone healing or bone synthesis; e.g., the compositions can be administered to fracture fixation (such as fracture healing) in broken bones, or treatment of osteoporotic bone (i.e., to promote osteogenesis and strengthen the bone). The compositions are also useful to strengthen or repair osteoporotic bone, where there is not a lot of nascent bone material to start with. In this exemplary embodiment, the compositions may promote accelerated osteogenesis within the osteoporotic bone, thereby strengthening the bone. This can be accomplished with little or no destruction of the osteoporotic bone; e.g., the compositions may be simply coated onto the osteoporotic bone, or alternatively, used to fill in defects. In addition, the compositions can be used to reconstruct a segmental defect in the case of missing bone, e.g., following tumor resection, polytrauma, or combinations thereof. In general, the compositions can be administered anywhere it is desired to promote osteogenesis within or adjacent to bone.

In some embodiments, the CSA is administered with an antimicrobial. In some embodiments, the antimicrobial is a CSA. In other embodiments, the antimicrobial is a CSA that facilitates the treatment of bone disease or a broken bone. In some embodiments, a single CSA is administered that facilitates antimicrobial effects and treats bone diseases or broken bones.

In some embodiments, the CSA is administered with additional compounds that provide therapeutic effects towards bone diseases or broken bones. In some embodiments, the CSA is administered with one or more bisphosphonates. Examples of bisphosphonates include Etidronate, Elodronate, Tiladronate, Pamidronate, Neridronate, Olpadronate, Alendronate, Ibandronate, Residronate, and/or Zoledronate. In some embodiments, the CSA is administered with calcium and/or vitamin D. In some embodiments, the CSA is administered with compounds for the treatment of osteoporosis. In some embodiments, the CSA is administered with Teriparatide, strontium ranelate, raloxifene, and/or Denosumab.

Other embodiments include kits comprising CSA compositions and instructions on disclosed methods. In some embodiments, kits include compounds (e.g., CSA), combination compositions and pharmaceutical compositions/formulations thereof, packaged into a suitable packaging material. In one embodiment, a kit includes packaging material, a CSA, and instructions. In various aspects, the instructions are for administering the CSA to: provide a subject with protection against a pathogenesis; treat a subject for pathogenesis; decrease susceptibility of a subject to a pathogenesis; or decrease or prevent an adverse side effect caused by a pathogenesis. The pathogenesis includes bone diseases and broken bones as described above.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with an osteogenesis agent or treatment or drug, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

One of ordinary skill in the art to which these exemplary embodiments belong will understand that the compositions may be administered in numerous ways. For example, administration may mean simply applying the compositions to a bone directly. In some exemplary embodiments, administration may be enteral, parenteral, or topical. Other exemplary routes of administration for contact or in vivo delivery which a compound can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, and/or intralymphatic.

The delivery forms can be homogeneous, e.g., forms in which the composition is in solution, or heterogeneous, e.g., forms in which the composition is contained within liposomes or microspheres. The forms can produce an immediate effect, and can alternatively, or additionally, produce an extended effect. For example, liposomes, or microspheres, or other similar means of providing an extended release of the composition, can be used to extend the period during which the composition is exposed to the targeted area; non-encapsulated compositions can also be provided for an immediate effect.

In some embodiments, the composition or method includes administering a CSA from a pharmaceutically acceptable device(s) such as bandages, surgical dressings, gauzes, adhesive strips, surgical staples, clips, hemostats, intrauterine devices, sutures, trocars, catheters, tubes, and implants. In some embodiments, the implant is a pill, pellet, rod, screw, wafer, disc, sponge and/or tablet. In some embodiments, the sponge is an absorbable collagen sponge. The devices can deliver the composition to a targeted area for a desired period of time. In some exemplary embodiments, the composition may be incorporated into a medical device coating. In some embodiments, the coating contains 0.1 weight %, 1 weight %, 5 weight %, 10 weight %, 15 weight %, 20 weight %, 25 weight %, 50 weight %, about any of the aforementioned numbers, and/or a range bounded by any two of the aforementioned numbers.

Devices according to the disclosure can be prepared according to known methods, and can include, or be made from, polymeric material. In some instances, the polymeric material will be an absorbable material and in other instances, a non-absorbable material, or in other instances a resorbable material. Devices can, of course, include absorbable, non-absorbable, resorbable materials, and combinations thereof.

Absorbable materials can be synthetic materials and non-synthetic materials. Absorbable synthetic materials include, but are not limited to, cellulosic polymers, glycolic acid polymers, methacrylate polymers, ethylene vinyl acetate polymers, ethylene vinyl alcohol copolymers, polycaptrolactam, polyacetate, copolymers of lactide and glycolide, polydioxanone, polyglactin, poliglecaprone, polyglyconate, polygluconate, and combinations thereof. Absorbable non-synthetic materials include, but are not limited to, catgut, cargile membrane, fascia lata, gelatin, collagen, and combinations thereof.

Nonabsorbable synthetic materials include, but are not limited to nylons, rayons, polyesters, polyolefins, and combinations thereof. Non-absorbable non-synthetic materials include, but are not limited to, silk, dermal silk, cotton, linen, and combinations thereof.

Combinations of the foregoing devices and carriers/vehicles are also envisioned. For example, a CSA gel or ointment can be impregnated into a bandage or wound dressing for delivery of the CSA to a targeted location. As another example, an implantable absorbable device can be loaded with a CSA solution and release the solution from the device over a period as desired. The physical form used to deliver the CSA is not critical and the choice or design of such devices is well within the level of skill of one in the art.

It may be desirable to provide for other conditions in the practice of the present methods. For example, it may be desirable to ensure that the target region is sufficiently oxygenated; generally, it is sufficient that atmospheric oxygen be present. It also may be desirable to maintain a desired level of moisture and a particular temperature; in some embodiments, a warm, moist environment is desirable. While not required, it may also be desirable to establish or maintain a sterile environment.

Additionally, it may be desirable to include other therapeutically beneficial agents in the formulation. For example, the vehicles or carriers may also include humectants or moisturizers to maintain a desired moisture level in the treated area. Other possibilities include drugs such as anesthetics or antibiotics, which provide other desired effects. Again, the possibilities are unlimited and are left to the practitioner. In some exemplary embodiments the composition may comprise a second CSA for purposes for which CSAs are known to serve.

Dosages

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Compounds (e.g., CSAs), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 13 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Localized delivery is also contemplated, including but not limited to delivery techniques in which the compound is implanted, injected, infused, or otherwise locally delivered. Localized delivery is characterized by higher concentrations of drug at the site of desired action (e.g., the bone or break to be treated) versus systemic concentrations of the drug. Well-known localized delivery forms can be used, including long-acting injections; infusion directly into the site of action; depot delivery forms; controlled or sustained delivery compositions; transdermal patches; infusion pumps; and the like. The CSA can further be incorporated into a biodegradable or bioerodible material or be put into or on a medical device.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects, the therapeutic indication, and the mode of administration. Alternatively dosages may be based and calculated upon the surface area of the patient, as understood by those of skill in the art. Although the exact dosage will be determined on a drug-by-drug basis, some generalizations regarding the dosage can be made. The dosage regimen for a human patient may be, for example, a dose of between about 0.1 µg/g to about 50 µg/g for local delivery. In some embodiments, the dosage regimen for local or systemic delivery (based on the weight of the patient) may be about 1 µg/g, 5 µg/g, 10 µg/g, 50 µg/g, 100 µg/g, 200 µg/g, 500 µg/g, 750 µg/g, 1000 µg/g, or less than any of the aforementioned numbers, or a range bounded by any two of the aforementioned numbers. In some embodiments, between about 0.001 mg to about 3000 mg of the active ingredient is delivered is administered locally or systemically. In some embodiments, about 5-15 mg of active ingredient is administered locally or systemically. In other embodiments, about 0.001 mg, 0.01 mg, 0.1 mg, 1 mg, 5 mg, 10 mg, 15 mg, 25 mg, 50 mg, 100 mg, 500 mg, 1000 mg, or less than any of the aforementioned numbers, or a range bounded by any two of the aforementioned numbers is administered locally or systemically. The dosage may be a single one or a series of two or more given in the course of one or more days, as is needed by the subject. In some embodiments, the compounds will be administered for a period of continuous therapy, for example for a week or more, or for months or years.

In instances where animal and/or human dosages for different compounds having been established for at least some condition, those same dosages may be used, or dosages that are between about 0.1% and 500%, more preferably between about 25% and 250% of the established animal and/or human dosage. For examples, dosages for INFUSE® BMP-2 and/or OP-1 BMP-7 are known and can be used to infer dosages for use in the disclosed embodiments. Where no animal and/or human dosage is established, as will be the case for newly-discovered pharmaceutical compositions, a suitable animal and/or human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Kits

Kits comprising the tissue treatment compositions and instructions for performing such methods are also disclosed. The disclosure also provides kits including compounds (e.g., CSA), combination compositions and pharmaceutical compositions/formulations thereof, packaged into a suitable packaging material. In one embodiment, a kit includes packaging material, a CSA, and instructions. In various aspects, the instructions are for administering the CSA to enhance bone growth and/or treat a broken bone in a subject.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more compounds alone or in combination with growth factors, optionally sterile.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

EXAMPLES

BMP Regulation

SABisosciences custom array plates (Cat#PAHS-026) were used to measure BMP expression. These array plates are validated for efficiency when used at recommended conditions and reagents. On day 1, primary human MSC cells were plated at 200,000 cell/well using 6-well plates with 10% FBS, Penicillin and Streptomycin 10 mL per Liter, in recommended media. Only early passages of cells were used.

On day 2, cells were treated with compounds dissolved in DMSO diluted 1:1000 or more to avoid solvent effects. A non-treated negative control group was evaluated (FIG. 1, "Control Group") along with a positive control group containing PS1 at 0.1 µM (FIG. 1, "Group 1"). Final testing concentration for CSA-90 was 5.0 µM (FIG. 1, "Group 2"), 2.5 µM (FIG. 1, "Group 3"), and 1.2 µM (FIG. 1, "Group 4"). Treatment lasted 8 hours, followed by RNA isolation using a QIAGEN Miniprep Kit. RNA was measured at 260/280 nm using NanoDrop2000 and normalized to 250 ng. cDNA preparation was done using QIAGEN First Strand kit.

The positive control containing PS1 (Proteasome inhibitor-1) at 0.1 µM produced a 3 fold up-regulation of BMP-2 mRNA compared to the control. Additional gene regulation data for PS1 at 0.1 µM is provided in Table 1.

TABLE 1

Gene Regulation of PS1 v. Untreated Control Group

| Gene Symbol | Fold Up-Regulation | Descriptive name |
|---|---|---|
| MSX1 | 6.2916 | Msh homeobox 1 |
| CSF2 | 6.205 | Colony stimulating factor 2 (granulocyte-macrophage) |
| MMP8 | 3.7453 | Matrix metallopeptidase 8 (neutrophil collagenase) |
| BMP-2 | 3.0816 | Bone morphogenetic protein 2 |
| BMP-6 | 2.642 | Bone morphogenetic protein 6 |
| TGFB3 | 2.2234 | Transforming growth factor, beta 3 |
| TGFBR1 | 2.0059 | Transforming growth factor, beta receptor 1 |
| PHEX | 1.9871 | Phosphate regulating endopeptidase homolog, X linked |
| TNF | 1.8055 | Tumor necrosis factor (TNF superfamily, member 2) |
| COL10A1 | 1.5421 | Collagen, type X, alpha 1 |
| IGF1 | 1.5067 | Insulin-like growth factor 1 (somatomedin C) |
| ICAM1 | 1.5053 | Intercellular adhesion molecule 1 |
| SERPIN H1 | 1.4764 | Serpin peptidase inhibitor, clade H (heat shock protein 47), member 1, (collagen binding protein 1) |
| TUFT1 | 1.4326 | Tuftelin 1 |
| FGF2 | 1.3957 | Fibroblast growth factor 2 (basic) |
| MMP10 | 1.3516 | Matrix metallopeptidase 10 (stromelysin 2) |
| ITGAM | 1.3319 | Integrin, alpha M (complement component 3 receptor 3 subunit) |
| ITGA1 | 1.325 | Integrin, alpha 1 |
| SMAD4 | 1.3022 | SMAD family member 4 |
| PPC | 1.2774 | Positive PCR Control |
| COMP | 1.2648 | Cartilage oligomeric matrix protein |
| PPC | 1.2343 | Positive PCR Control |
| COL15A1 | 1.2144 | Collagen, type XV, alpha 1 |
| SCARB1 | 1.1791 | Scavenger receptor class B, member 1 |
| ITGB1 | 1.1614 | Integrin, beta 1 (fibronectin receptor, beta polypeptide, antigen CD29 includes MDF2, MSK12) |
| GAPDH | 1.161 | Glyceraldehyde-3-phosphate dehydrogenase |
| RTC | 1.1269 | Reverse Transcription Control |
| BMP-5 | 1.124 | Bone morphogenetic protein 5 |
| CALCR | 1.124 | CALCITONIN RECEPTOR |
| DMP1 | 1.124 | Dentin matrix acidic phosphoprotein 1 |
| DSPP | 1.124 | Dentin sialophosphoprotein |
| ENAM | 1.124 | Enamelin |
| GDF10 | 1.124 | Growth differentiation factor 10 |
| HGDC | 1.124 | Human Genomic DNA Contamination |
| ANXA5 | 1.1236 | Annexin A5 |
| TFIP11 | 1.1041 | Tuftelin interacting protein 11 |
| PPC | 1.1022 | Positive PCR Control |
| FN1 | 1.099 | Fibronectin 1 |
| COL5A1 | 1.0927 | Collagen, type V, alpha 1 |
| COL12A1 | 1.0767 | Collagen, type XII, alpha 1 |
| SMAD2 | 1.0462 | SMAD family member 2 |
| PDGFA | 1.0421 | Platelet-derived growth factor alpha polypeptide |
| RTC | 1.0199 | Reverse Transcription Control |
| TGFB2 | 1.0081 | Transforming growth factor, beta 2 |
| VEGFA | −1.0162 | Vascular endothelial growth factor A |
| CD36 | −1.0202 | CD36 molecule (thrombospondin receptor) |
| COL4A3 | −1.0619 | Collagen, type IV, alpha 3 (Goodpasture antigen) |
| RTC | −1.0657 | Reverse Transcription Control |
| COL1A2 | −1.0689 | Collagen, type I, alpha 2 |
| IGF1R | −1.0699 | Insulin-like growth factor 1 receptor |
| COL3A1 | −1.0806 | Collagen, type III, alpha 1 |
| ITGA2 | −1.0945 | Integrin, alpha 2 (CD49B, alpha 2 subunit of VLA-2 receptor) |
| FGFR1 | −1.0999 | Fibroblast growth factor receptor 1 |
| BMP-3 | −1.1038 | Bone morphogenetic protein 3 |
| NFKB1 | −1.1038 | Nuclear factor of kappa light polypeptide gene enhancer in B-cells 1 |
| VEGFB | −1.1191 | Vascular endothelial growth factor B |
| MMP2 | −1.1194 | Matrix metallopeptidase 2 (gelatinase A, 72 kDa gelatinase, 72 kDa type IV collagenase) |
| BMP-1 | −1.1214 | Bone morphogenetic protein 1 |
| BGN | −1.1323 | Biglycan |
| COL1A1 | −1.1935 | Collagen, type I, alpha 1 |
| IGF2 | −1.2388 | Insulin-like growth factor 2 (somatomedin A) |
| MMP9 | −1.2449 | Matrix metallopeptidase 9 (gelatinase B, 92 kDa gelatinase, 92 kDa type IV collagenase) |
| EGF | −1.2529 | Epidermal growth factor (beta-urogastrone) |
| FGFR2 | −1.2644 | Fibroblast growth factor receptor 2 |
| TGFB1 | −1.2644 | Transforming growth factor, beta 1 |
| CTSK | −1.2679 | Cathepsin K |
| SMAD1 | −1.2813 | SMAD family member 1 |
| FGF3 | −1.3257 | Fibroblast growth factor 3 (murine mammary tumor virus integration site (v-int-2) oncogene homolog) |
| AHSG | −1.3295 | Alpha-2-HS-glycoprotein |
| BGLAP | −1.3879 | Bone gamma-carboxyglutamate (gla) protein |
| ACTB | −1.4183 | Actin, beta |
| COL2A1 | −1.4242 | Collagen, type II, alpha 1 |
| ALPL | −1.4723 | Alkaline phosphatase, liver/bone/kidney |

TABLE 1-continued

Gene Regulation of PS1 v. Untreated Control Group

| Gene Symbol | Fold Up-Regulation | Descriptive name |
|---|---|---|
| COL11A1 | −1.4875 | Collagen, type XI, alpha 1 |
| FGF1 | −1.4948 | Fibroblast growth factor 1 (acidic) |
| VDR | −1.5248 | Vitamin D (1,25-dihydroxyvitamin D3) receptor |
| COL14A1 | −1.5279 | Collagen, type XIV, alpha 1 |
| EGFR | −1.8532 | Epidermal growth factor receptor (erythroblastic leukemia viral (v-erb-b) oncogene homolog, avian) |
| AMELY | −1.8864 | Amelogenin, Y-linked |
| ITGA3 | −1.8917 | Integrin, alpha 3 (antigen CD49C, alpha 3 subunit of VLA-3 receptor) |
| AMBN | −1.9272 | Ameloblastin (enamel matrix protein) |
| TWIST1 | −2.197 | Twist homolog 1 (Drosophila) |
| BMP-4 | −2.2148 | Bone morphogenetic protein 4 |
| CDH11 | −2.2309 | Cadherin 11, type 2, OB-cadherin (osteoblast) |
| STATH | −2.2674 | Statherin |
| TGFBR2 | −2.3752 | Transforming growth factor, beta receptor II (70/80 kDa) |
| VCAM1 | −2.406 | Vascular cell adhesion molecule 1 |
| CSF3 | −2.4364 | Colony stimulating factor 3 (granulocyte) |
| SMAD3 | −2.771 | SMAD family member 3 |
| FLT1 | −2.7821 | Fms-related tyrosine kinase 1 (vascular endothelial growth factor/vascular permeability factor receptor) |
| RUNX2 | −3.542 | Runt-related transcription factor 2 |

Figure 2:
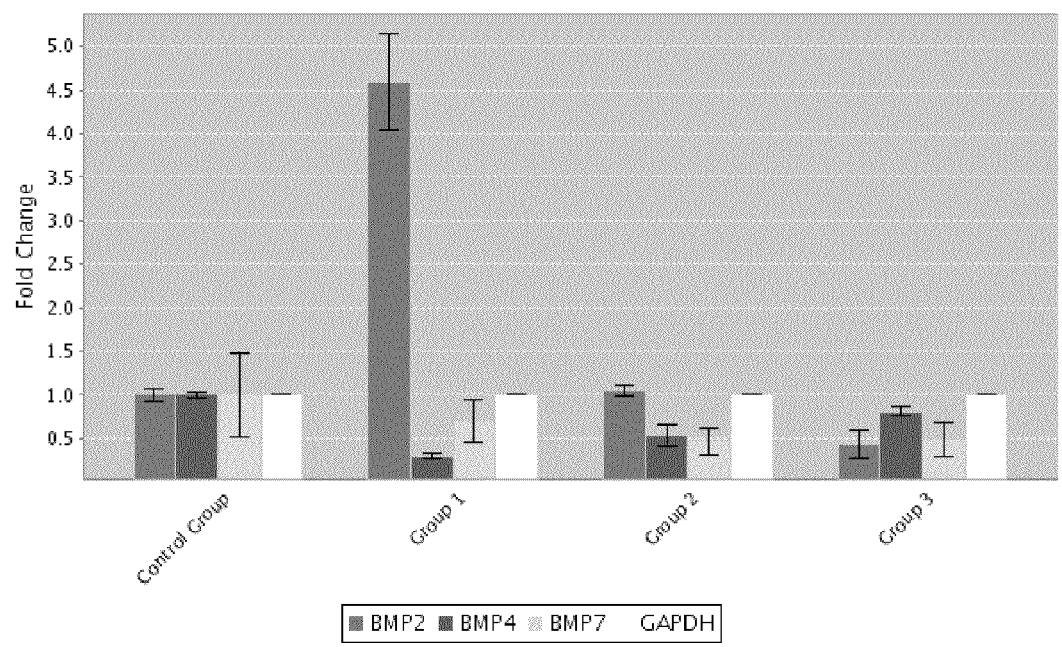
FIG. 2: Triplicate testing of BMP up-regulation in hMSC treated with CSA after 8 hours dosing.
Figure 3:
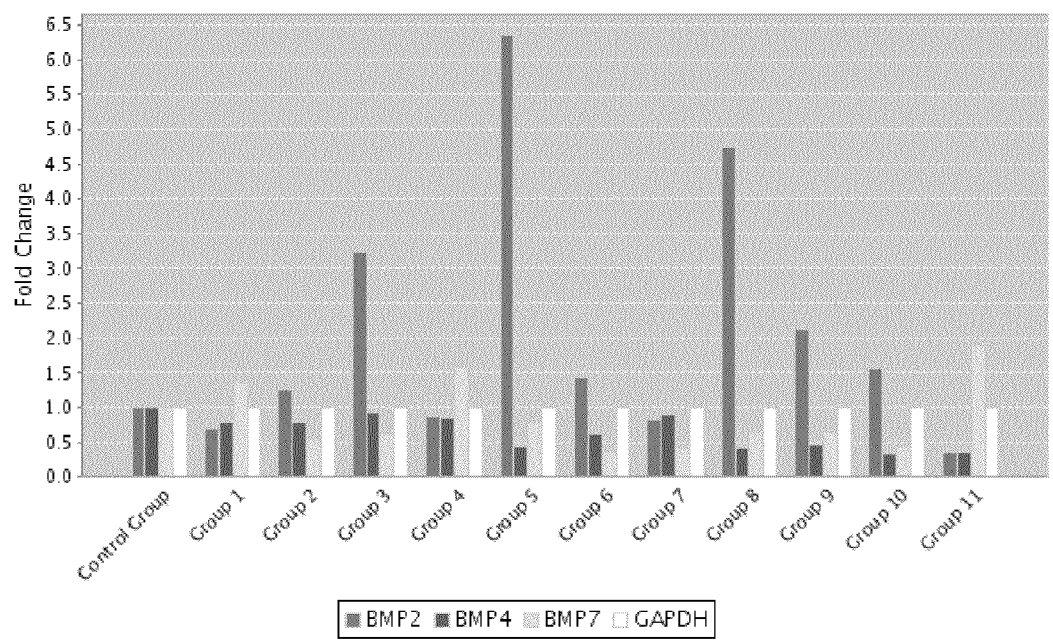
FIG. 3: BMP up-regulation in hMSC treated with CSAs 8, 13, 44, 54, 90, 92, 97, and 98 (Groups 1-8, respectively) after 8 hours dosing.

Repeating the experiment in triplicate afforded the results illustrated in FIG. 2, wherein the control group is untreated; Group 1 is CSA-90 at 5 μM; Group 2 is CSA-90 at 2.5 μM; and Group 3 is CSA-90 at 1.2 μM. Additional experiments were performed with hMSC treated with CSAs 8, 13, 44, 54, 90, 92, 97, and 98 (Groups 1-8, respectively; FIG. 3). CSA-90, along with other CSAs, effectively up-regulated BMP-2 mRNA expression (~6 fold up-regulation for CSA-90 at a 5 μM concentration). Additional gene regulation data for CSA-90 is provided in Table 2.

TABLE 2

Gene Regulation of CSA-90 v. Untreated Control Group

| Gene Symbol | Fold Up-Regulation | Descriptive name |
|---|---|---|
| IGF1 | 15.8816 | Insulin-like growth factor 1 (somatomedin C) |
| BMP-6 | 14.8826 | Bone morphogenetic protein 6 |
| BMP-2 | 6.7295 | Bone morphogenetic protein 2 |
| TGFB3 | 3.2853 | Transforming growth factor, beta 3 |
| CSF2 | 3.2231 | Colony stimulating factor 2 (granulocyte-macrophage) |
| TNF | 2.7072 | Tumor necrosis factor (TNF superfamily, member 2) |
| ITGAM | 2.5974 | Integrin, alpha M (complement component 3 receptor 3 subunit) |
| STATH | 2.5891 | Statherin |
| PPC | 2.3361 | Positive PCR Control |
| MMP10 | 2.1233 | Matrix metallopeptidase 10 (stromelysin 2) |
| BMP-5 | 2.1036 | Bone morphogenetic protein 5 |
| CALCR | 2.1036 | CALCITONIN RECEPTOR |
| DMP1 | 2.1036 | Dentin matrix acidic phosphoprotein 1 |
| DSPP | 2.1036 | Dentin sialophosphoprotein |
| ENAM | 2.1036 | Enamelin |
| GDF10 | 2.1036 | Growth differentiation factor 10 |
| HGDC | 2.1036 | Human Genomic DNA Contamination |
| MMP9 | 2.0169 | Matrix metallopeptidase 9 (gelatinase B, 92 kDa gelatinase, 92 kDa type IV collagenase) |
| PPC | 1.9116 | Positive PCR Control |
| IGF1R | 1.6854 | Insulin-like growth factor 1 receptor |
| TGFB2 | 1.619 | Transforming growth factor, beta 2 |
| ITGA2 | 1.6174 | Integrin, alpha 2 (CD49B, alpha 2 subunit of VLA-2 receptor) |
| RTC | 1.6043 | Reverse Transcription Control |
| COMP | 1.5909 | Cartilage oligomeric matrix protein |
| RTC | 1.5346 | Reverse Transcription Control |
| TGFBR1 | 1.5219 | Transforming growth factor, beta receptor 1 |
| RTC | 1.4817 | Reverse Transcription Control |
| AHSG | 1.4077 | Alpha-2-HS-glycoprotein |
| BMP-3 | 1.3888 | Bone morphogenetic protein 3 |
| ICAM1 | 1.3786 | Intercellular adhesion molecule 1 |
| VEGFA | 1.3548 | Vascular endothelial growth factor A |
| CSF3 | 1.3504 | Colony stimulating factor 3 (granulocyte) |
| ITGA1 | 1.2807 | Integrin, alpha 1 |
| VEGFB | 1.2749 | Vascular endothelial growth factor B |
| COL3A1 | 1.1521 | Collagen, type III, alpha 1 |
| COL15A1 | 1.1217 | Collagen, type XV, alpha 1 |
| EGFR | 1.0894 | Epidermal growth factor receptor (erythroblastic leukemia viral (v-erb-b) oncogene homolog, avian) |
| CTSK | 1.0843 | Cathepsin K |
| COL2A1 | 1.0817 | Collagen, type II, alpha 1 |
| COL14A1 | 1.0661 | Collagen, type XIV, alpha 1 |
| COL10A1 | 1.0439 | Collagen, type X, alpha 1 |
| NFKB1 | 1.0365 | Nuclear factor of kappa light polypeptide gene enhancer in B-cells 1 |
| AMELY | −1.008 | Amelogenin, Y-linked |
| MMP8 | −1.0189 | Matrix metallopeptidase 8 (neutrophil collagenase) |
| ANXA5 | −1.0287 | Annexin A5 |
| AMBN | −1.0298 | Ameloblastin (enamel matrix protein) |
| FGF2 | −1.0498 | Fibroblast growth factor 2 (basic) |
| GAPDH | −1.0501 | Glyceraldehyde-3-phosphate dehydrogenase |
| SMAD4 | −1.0529 | SMAD family member 4 |
| VCAM1 | −1.1098 | Vascular cell adhesion molecule 1 |
| BGLAP | −1.1336 | Bone gamma-carboxyglutamate (gla) protein |
| PDGFA | −1.1381 | Platelet-derived growth factor alpha polypeptide |
| MSX1 | −1.1393 | Msh homeobox 1 |
| RUNX2 | −1.1998 | Runt-related transcription factor 2 |
| SMAD2 | −1.2016 | SMAD family member 2 |
| SMAD1 | −1.2436 | SMAD family member 1 |
| ITGB1 | −1.3007 | Integrin, beta 1 (fibronectin receptor, beta polypeptide, antigen CD29 includes MDF2, MSK12) |
| TGFB1 | −1.3031 | Transforming growth factor, beta 1 |
| COL12A1 | −1.366 | Collagen, type XII, alpha 1 |
| EGF | −1.3949 | Epidermal growth factor (beta-urogastrone) |
| BMP-1 | −1.4719 | Bone morphogenetic protein 1 |
| FN1 | −1.4863 | Fibronectin 1 |
| COL1A2 | −1.525 | Collagen, type I, alpha 2 |
| FGF3 | −1.5325 | Fibroblast growth factor 3 (murine mammary tumor virus integration site (v-int-2) oncogene homolog) |
| FGFR1 | −1.5568 | Fibroblast growth factor receptor 1 |
| MMP2 | −1.6002 | Matrix metallopeptidase 2 (gelatinase A, 72 kDa gelatinase, 72 kDa type IV collagenase) |
| COL5A1 | −1.603 | Collagen, type V, alpha 1 |
| TFIP11 | −1.6592 | Tuftelin interacting protein 11 |
| TWIST1 | −1.6813 | Twist homolog 1 (Drosophila) |
| FGF1 | −1.7551 | Fibroblast growth factor 1 (acidic) |
| TGFBR2 | −1.7799 | Transforming growth factor, beta receptor II (70/80 kDa) |
| COL1A1 | −1.9589 | Collagen, type I, alpha 1 |
| PHEX | −2.0881 | Phosphate regulating endopeptidase homolog, X-linked |
| ITGA3 | −2.1172 | Integrin, alpha 3 (antigen CD49C, alpha 3 subunit of VLA-3 receptor) |
| FLT1 | −2.1823 | Fms-related tyrosine kinase 1 (vascular endothelial growth factor/vascular permeability factor receptor) |
| BGN | −2.2679 | Biglycan |
| CD36 | −2.3276 | CD36 molecule (thrombospondin receptor) |
| CDH11 | −2.6119 | Cadherin 11, type 2, OB-cadherin (osteoblast) |
| IGF2 | −2.6412 | Insulin-like growth factor 2 (somatomedin A) |
| SERPIN H1 | −2.6434 | Serpin peptidase inhibitor, clade H (heat shock protein 47), member 1, (collagen binding protein 1) |
| SCARB1 | −2.7137 | Scavenger receptor class B, member 1 |

TABLE 2-continued

Gene Regulation of CSA-90 v. Untreated Control Group

| Gene Symbol | Fold Up-Regulation | Descriptive name |
|---|---|---|
| COL11A1 | −2.8055 | Collagen, type XI, alpha 1 |
| SMAD3 | −2.8152 | SMAD family member 3 |
| FGFR2 | −3.1961 | Fibroblast growth factor receptor 2 |
| BMP-4 | −3.7558 | Bone morphogenetic protein 4 |
| ACTB | −4.1173 | Actin, beta |
| TUFT1 | −4.5431 | Tuftelin 1 |
| ALPL | −5.8397 | Alkaline phosphatase, liver/bone/kidney |
| VDR | −6.6007 | Vitamin D (1,25-dihydroxyvitamin D3) receptor |
| COL4A3 | −9.7105 | Collagen, type IV, alpha 3 (Goodpasture antigen) |

In Vitro Analysis

Figure 4:
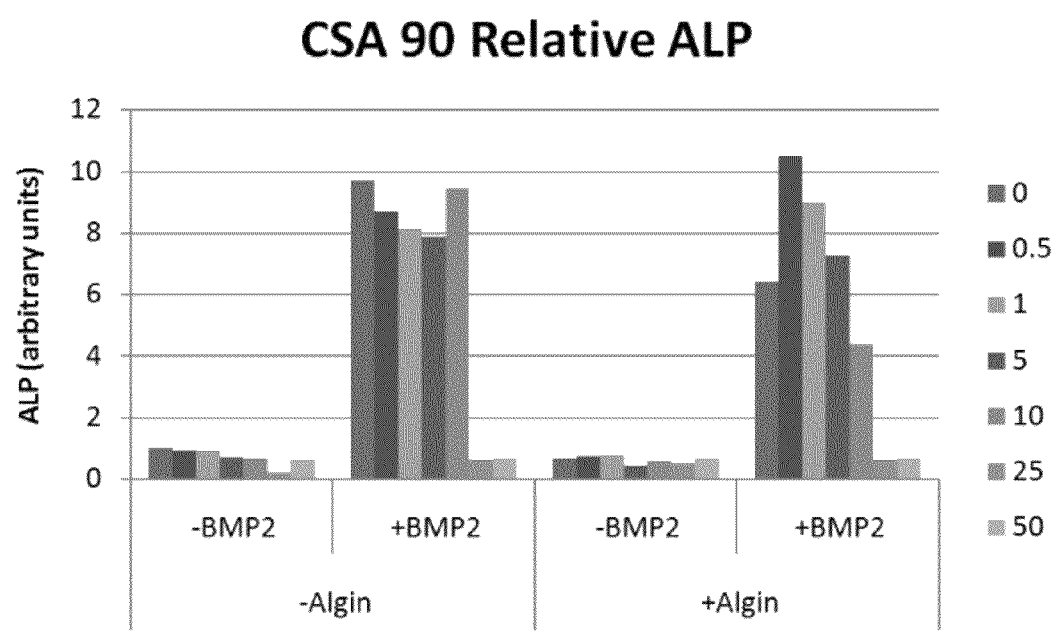
FIG. 4: MC3T3-E1 cells treated with or without rhBMP-2, 0-50 μM CSA-90, and with or without sodium alginate.

MC3T3-E1 cells at day 4 of differentiation were treated with or without 200 ng/mL rhBMP-2 (recombinant human BMP-2), 0-50 μM CSA-90, and with or without 50 μM sodium alginate. Quantitative spectroscopic ALP (alkaline phosphatase) assays were performed in on multiple wells and normalized to viable cell number. Experimental assays were carried out twice independently. Data for this analysis is provided in FIG. 4 (from left to right 0, 0.5, 1, 5, 10, 25, and 50 μM CSA-90 were tested with or without BMP-2 and Algin). Comparable results were seen with CSA-13.

Figure 5:
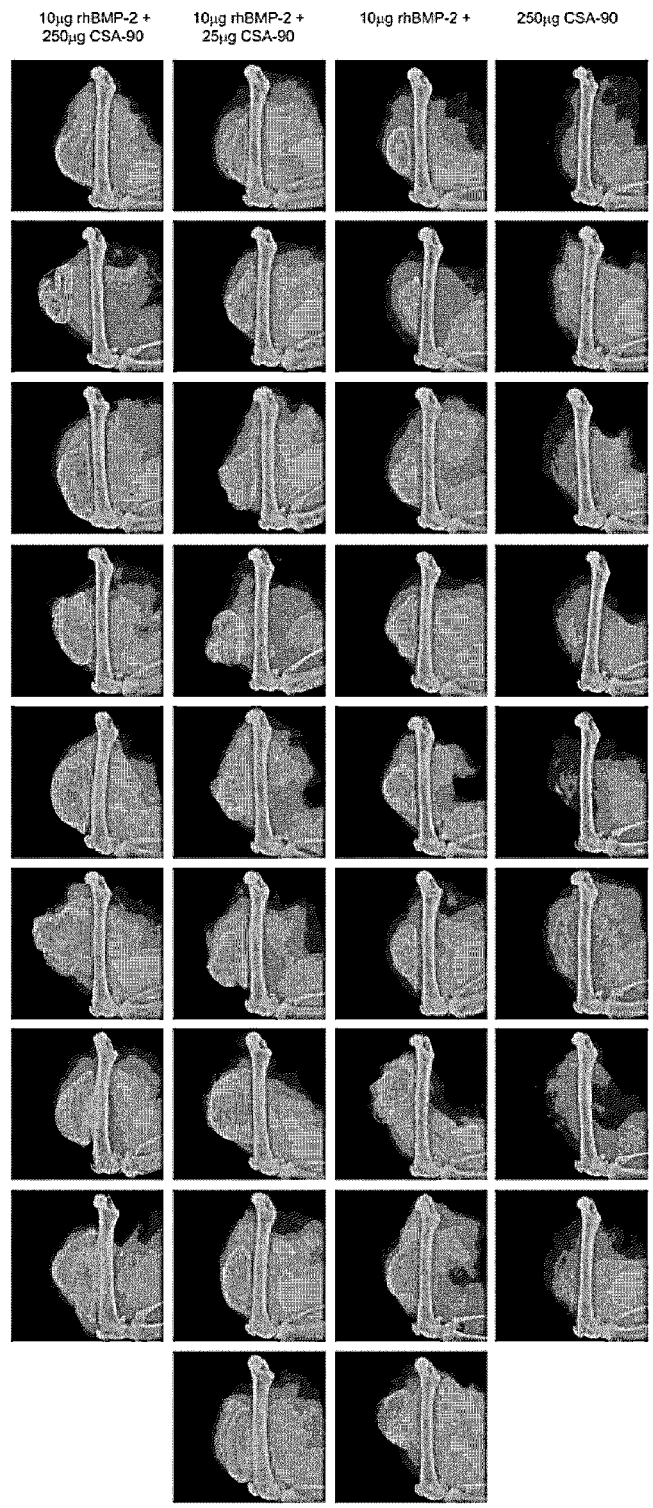
FIG. 5: X-ray analysis of mice quadriceps treated with rhBMP-2 and/or CSA-90.

In Vivo Analysis:

10 μg rhBMP-2 was implanted into the quadriceps of mice with 0, 25 μg, or 250 μg CSA-90. A control group received 250 μg CSA-90 alone (without rhBMP-2). Bone was allowed to form ectopically over 3 weeks. Specimens were then harvested for XR (FIG. 5) and microCT (FIG. 7).

Figure 6:
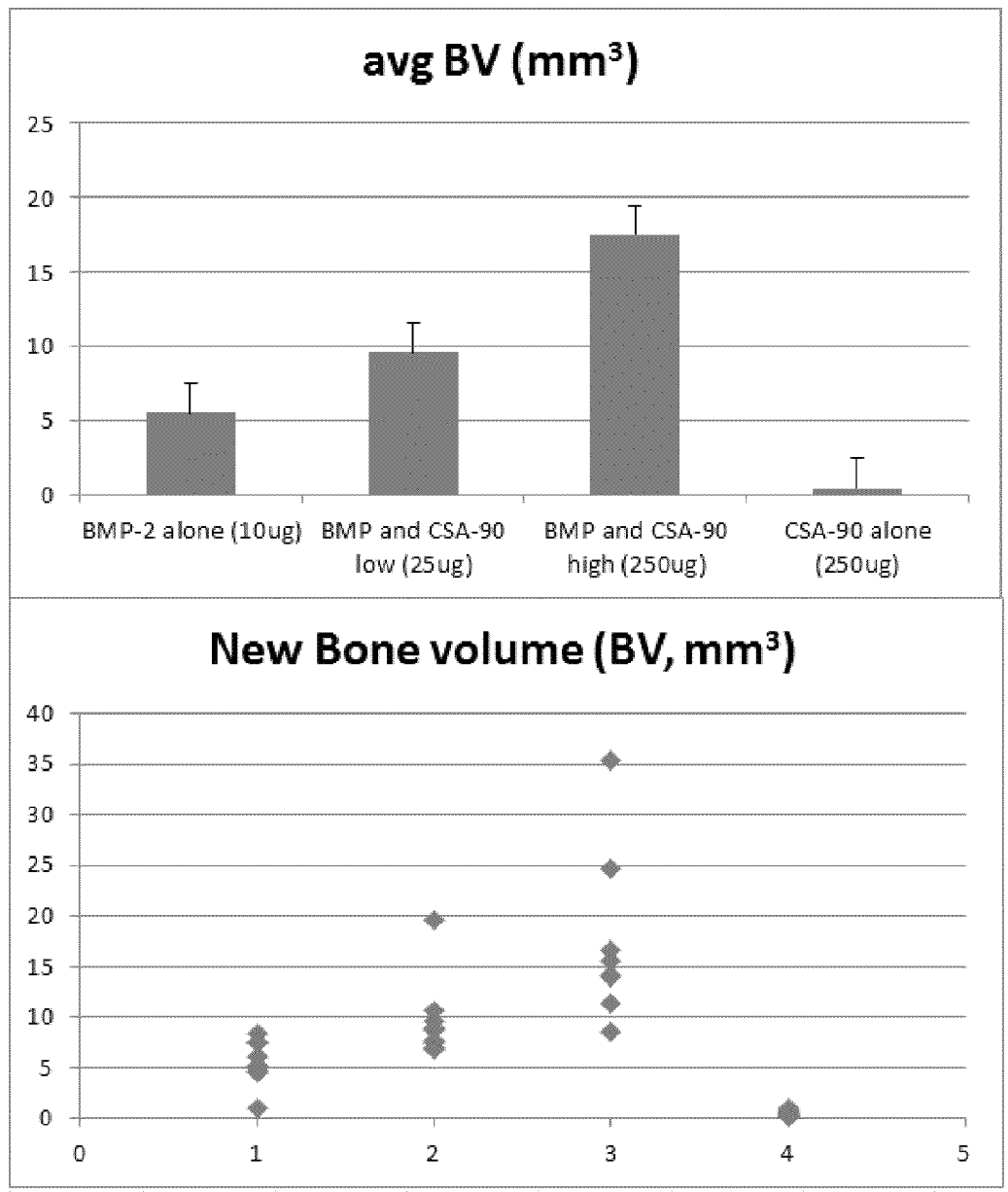
FIG. 6: Bone volume increase resulting from treatment with rhBMP-2 and/or CSA-90.

MicroCT scans were performed on all samples using a Skyscan 1174 microCT scanner. Scanning data confirmed increases in bone volume (BV) with the addition of CSA-90 (See FIG. 6). Based on parametric tests comparing 25 μg CSA90 and 250 μg CSA90 with rhBMP-2 alone, these increases were statistically significant (*P=0.02, P<0.01 respectively). Using nonparametric rank tests, the increases were also statistically significant (*P<0.01 for both groups). This data indicates that the addition of CSA-90 increased the ectopic bone volume induced by rhBMP-2 treatment by about 3.2 fold.

Figure 7:
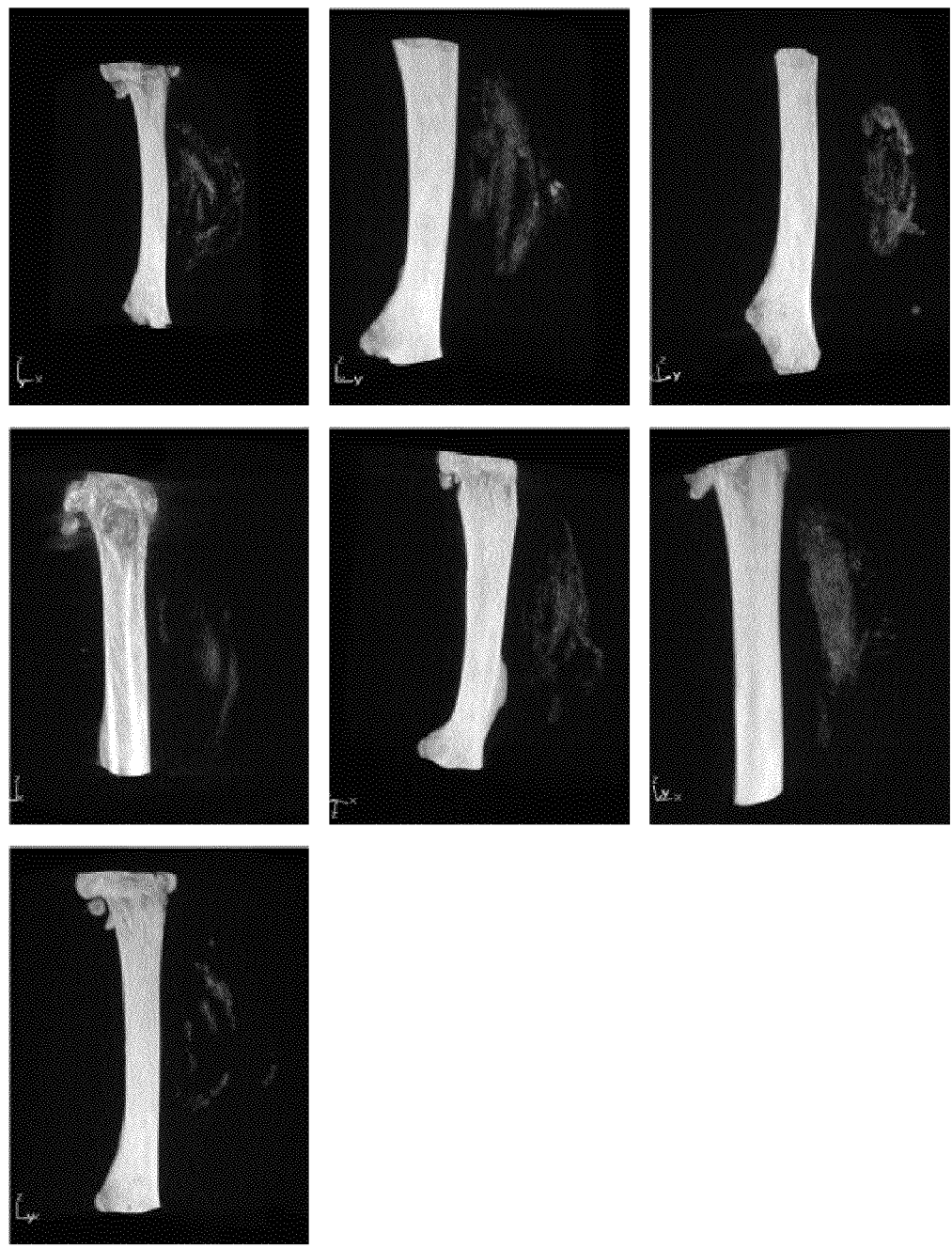
FIG. 7: microCT scan for CSA-90 delivered in a muscle pouch model.

Moreover, CSA-90 alone (250 μg) delivered in the muscle pouch model appears to also result in bone formation (See FIG. 7, indicating de-novo bone formation exemplified by a fine network of mineralized tissue).

Conclusion

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of promoting osteogenesis in a subject in need of treatment for a bone disease or healing a broken bone, comprising:
   identifying a subject in need of treatment for a bone disease or healing a broken bone; and
   administering to the subject an amount ranging from about 0.1 μg/g to about 50 μg/g of body weight and/or an amount ranging from about 0.001 mg to about 1000 mg of at least one cationic steroid antimicrobial (CSA) of Formula V, or a pharmaceutically acceptable salt thereof:

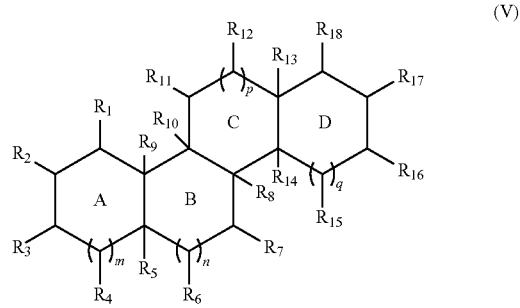

(V)

wherein
rings A, B, C, and D are independently saturated;
m, n, p, and q are independently 0 or 1;
$R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and substituted or unsubstituted ($C_1$-$C_6$) alkyl;
$R_3$, $R_7$, $R_{12}$, and $R_{18}$ are independently selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, linking group attached to a second CSA, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl) aminoalkyl, substituted or unsubstituted C-carboxy($C_1$-$C_{18}$) alkyl, $H_2N$—HC($Q_5$)-C(O)—O—, $H_2N$—HC($Q_5$)-C(O)—N(H)—, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O—, substituted or unsubstituted ($C_1$-$C_{18}$) guanidinoalkyloxy, substituted or unsubstituted ($C_1$-$C_{18}$) quaternaryammoniumalkylcarboxy, and substituted or unsubstituted ($C_1$-$C_{18}$) guanidinoalkyl carboxy, where $Q_5$ is a side chain of an amino acid and P.G. is an amino protecting group;
provided that at least two of $R_3$, $R_7$, $R_{12}$ and $R_{18}$ are independently selected from the group consisting of aminoalkyloxy, aminoalkylcarboxy, alkylaminoalkyl, and di(alkyl)aminoalkyl.

2. The method of claim 1, further comprising administering to the subject at least one growth factor.

3. The method of claim 2, wherein the growth factor is BMP-2 or rhBMP-2.

4. The method of claim 1, wherein the at least one CSA, or a pharmaceutically acceptable salt thereof, facilitates healing of a trauma injury.

5. The method of claim 1, further comprising administering to the subject an antimicrobial agent to treat or prevent infection.

6. The method of claim 5, wherein the at least one CSA, or a pharmaceutically acceptable salt thereof, treats the bone disease or heals the broken bone and treats or prevent infection.

7. The method of claim 1, wherein the at least one CSA, or a pharmaceutically acceptable salt thereof, is administered from a pharmaceutically acceptable device selected from the group consisting of bandages, surgical dressings, gauzes, adhesive strips, surgical staples, clips, hemostats, intrauterine devices, sutures, trocars, catheters, tubes, and implants.

8. The method of claim 7, wherein the implant is selected from the group consisting of pills, pellets, rods, screws, wafers, discs, sponges, and tablets.

9. The method of claim 1, wherein the bone disease is selected from the group consisting of bone resorption, osteoarthritis, osteoporosis, osteomalacia, osteitis fibrosa cystica, osteochondritis dissecans, osteomalacia, osteoblastogenesis, osteomyelitis, osteopenia, osteonecrosis, and porotic hyperostosis.

10. The method of claim 1, wherein the broken bone results from one or more of a traumatic fracture; a critical sized bone defect; distraction osteogenesis; spine fusion surgery; joint replacement; an orthopaedic implant; or a biopsy.

11. The method of claim 1, wherein the at least one CSA, or a pharmaceutically acceptable salt thereof, is selected from the compound of Formula (I):

(I)

12. The method of claim 11, wherein
$R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted C-carboxy($C_1$-$C_{18}$)alkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and
$R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

13. The method of claim 11, wherein $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted C-carboxy($C_1$-$C_{18}$)alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy.

14. The method of claim 13, wherein $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

15. The method of claim 14, wherein
$R_3$, $R_7$, and $R_{12}$ are independently selected from the group consisting of aminoalkyloxy and aminoalkylcarboxy; and
$R_{18}$ is selected from the group consisting of alkylaminoalkyl; alkoxycarbonylalkyl; alkylcarbonyloxyalkyl; di(alkyl)aminoalkyl; C-carboxyalkyl; alkylaminoalkyl; alkyoxycarbonylalkyl; and alkylcarboxyalkyl.

16. The method of claim 4, wherein $R_3$, $R_7$, and $R_{12}$ are the same.

17. The method of claim 16, wherein $R_3$, $R_7$, and $R_{12}$ are aminoalkyloxy.

18. The method of claim 3, wherein $R_{18}$ is alkylaminoalkyl.

19. The method of claim 2, wherein $R_{18}$ is alkoxycarbonylalkyl.

20. The method of claim 1, wherein $R_{18}$ is di(alkyl)aminoalkyl.

21. The method of claim 1, wherein $R_{18}$ is alkylcarboxyalkyl.

22. The method of claim 15, wherein $R_3$, $R_7$, and $R_{12}$ are aminoalkylcarboxy.

23. The method of claim 15, wherein $R_{18}$ is alkylaminoalkyl.

24. The method of claim 15, wherein $R_{18}$ is alkoxycarbonylalkyl.

25. The method of claim 15, wherein $R_{18}$ is di(alkyl)aminoalkyl.

26. The method of claim 15, wherein $R_{18}$ is alkylcarboxyalkyl.

27. The method of claim 14, wherein $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkylcarbonyl-$C_4$-alkyl; di-($C_5$-alkyl)amino-$C_5$-alkyl; C-carboxy-$C_4$-alkyl; $C_{13}$-alkylamino-$C_5$-alkyl; $C_6$-alkoxy-carbonyl-$C_4$-alkyl; and $C_6$-alkyl-carboxy-$C_4$-alkyl.

28. The method of claim 11, wherein the at least one CSA, or a pharmaceutically acceptable salt thereof, is selected from the compound of Formula (Ia):

(Ia)

29. The method of claim 28, wherein the at least one CSA, or a pharmaceutically acceptable salt thereof, is selected from the group consisting of:
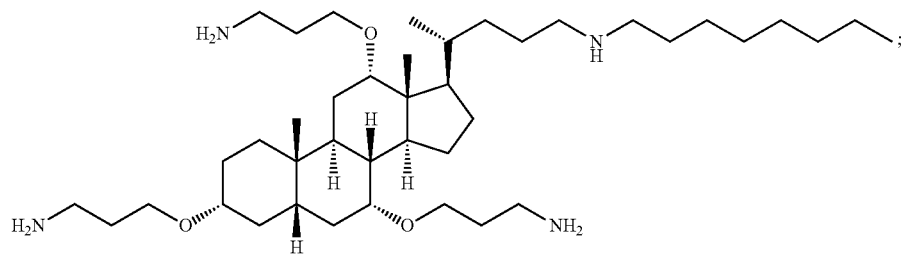
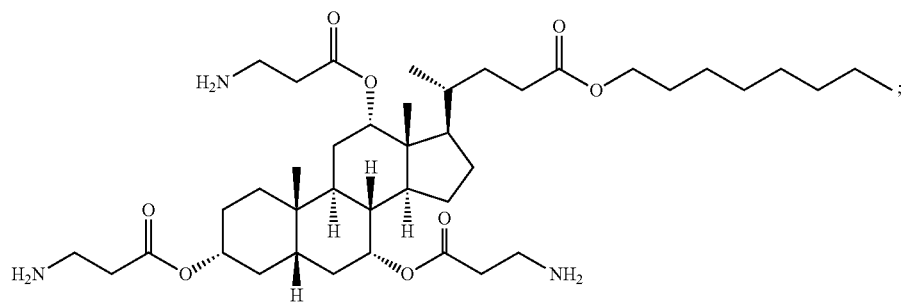
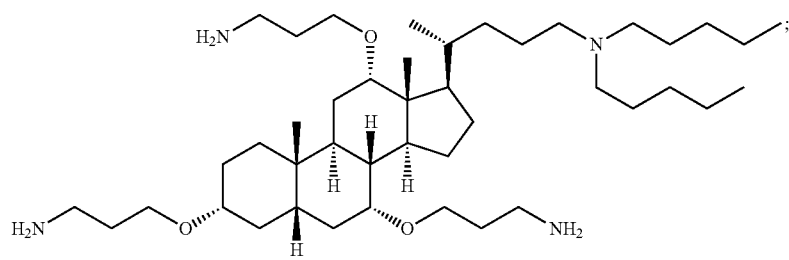
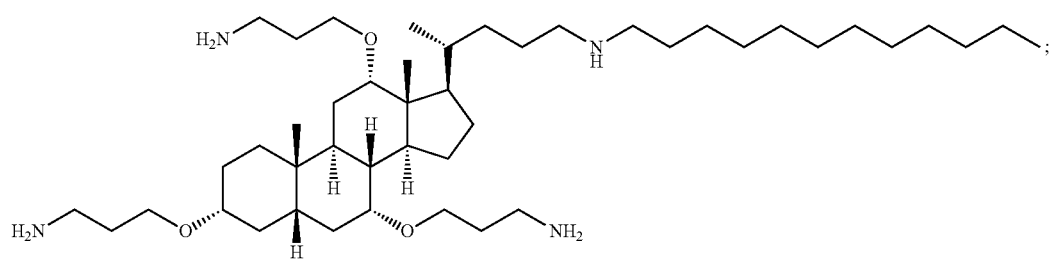
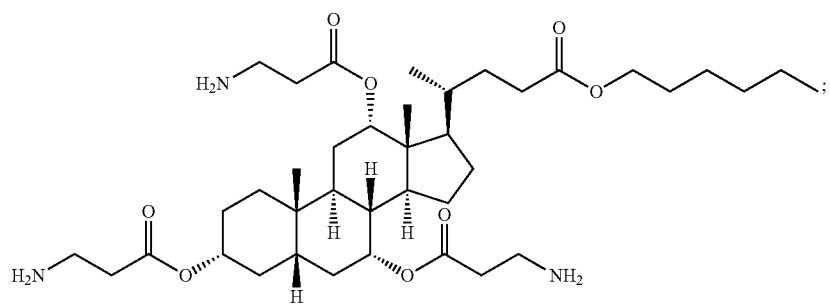
and pharmaceutically acceptable salts thereof.

30. The method of claim 29, wherein the compound of Formula (la), or a pharmaceutically acceptable salt thereof, is

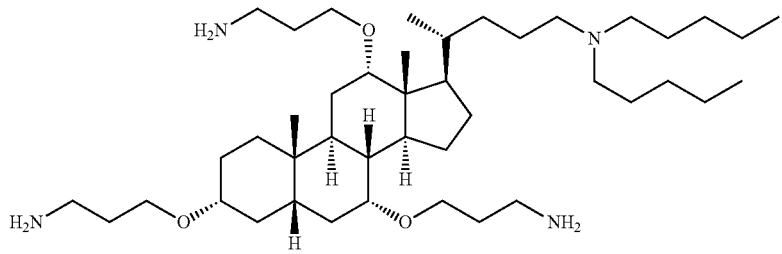

or a pharmaceutically acceptable salt thereof.

31. The method of claim 1, wherein the pharmaceutically acceptable salt is a hydrochloride salt.

32. The method of claim 31, wherein the pharmaceutically acceptable salt is a tri-hydrochloride salt.

33. A method of promoting osteogenesis in a subject in need of treatment for a bone disease or healing a broken bone, comprising:
identifying a subject in need of treatment for a bone disease or healing a broken bone; and
administering to the subject, by means of a pharmaceutically acceptable device, an effective amount of at least one cationic steroid antimicrobial (CSA) of Formula V, or a pharmaceutically acceptable salt thereof, and wherein the pharmaceutically acceptable device or coating applied to the pharmaceutically acceptable device includes about 0.1% to about 50% by weight of the at least one CSA or a pharmaceutically acceptable salt thereof:

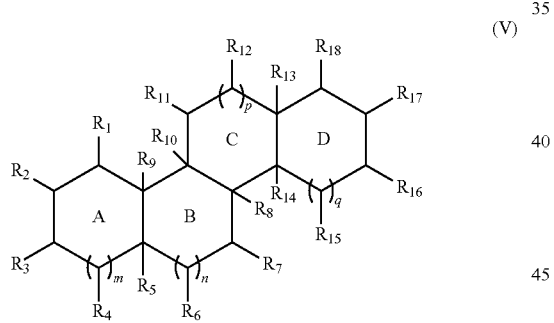

wherein
rings A, B, C, and D are independently saturated;
m, n, p, and q are independently 0 or 1;
$R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and substituted or unsubstituted ($C_1$-$C_6$) alkyl;

$R_3$, $R_7$, $R_{12}$, and $R_{18}$ are independently selected from the group consisting of hydrogen, hydroxyl, substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, substituted or unsubstituted ($C_1$-$C_{18}$) aminoalkyl, substituted or unsubstituted aryl, substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, linking group attached to a second CSA, substituted or unsubstituted ($C_1$-$C_{18}$) aminoalkyloxy, substituted or unsubstituted ($C_1$-$C_{18}$) aminoalkyloxy-($C_1$-$C_{18}$) alkyl, substituted or unsubstituted ($C_1$-$C_{18}$) aminoalkylcarboxy, substituted or unsubstituted ($C_1$-$C_{18}$) aminoalkylaminocarbonyl, substituted or unsubstituted ($C_1$-$C_{18}$) aminoalkylcarboxamido, substituted or unsubstituted di($C_1$-$C_{18}$ alkyl) aminoalkyl, substituted or unsubstituted C-carboxy($C_1$-$C_{18}$) alkyl, $H_2N$—$HC(Q_5)$-$C(O)$—$O$—, $H_2N$—$HC(Q_5)$-$C(O)$—$N(H)$—, substituted or unsubstituted ($C_1$-$C_{18}$) azidoalkyloxy, substituted or unsubstituted ($C_1$-$C_{18}$) cyanoalkyloxy, P.G.-HN—$HC(Q_5)$-$C(O)$—$O$—, substituted or unsubstituted ($C_1$-$C_{18}$) guanidinoalkyloxy, substituted or unsubstituted ($C_1$-$C_{18}$) quaternaryammoniumalkylcarboxy, and substituted or unsubstituted ($C_1$-$C_{18}$) guanidinoalkyl carboxy, where $Q_5$ is a side chain of an amino acid and P.G. is an amino protecting group;
provided that at least two of $R_3$, $R_7$, $R_{12}$ and $R_{18}$ are independently selected from the group consisting of aminoalkyloxy, aminoalkylcarboxy, alkylaminoalkyl, and di(alkyl)aminoalkyl.

34. The method of claim 33, wherein the at least one CSA, or a pharmaceutically acceptable salt thereof, is selected from the group consisting of:

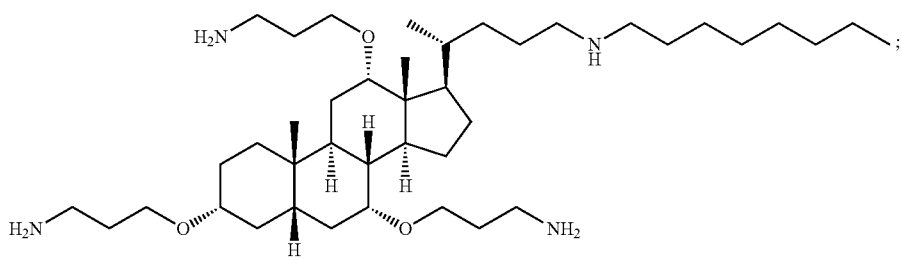

-continued

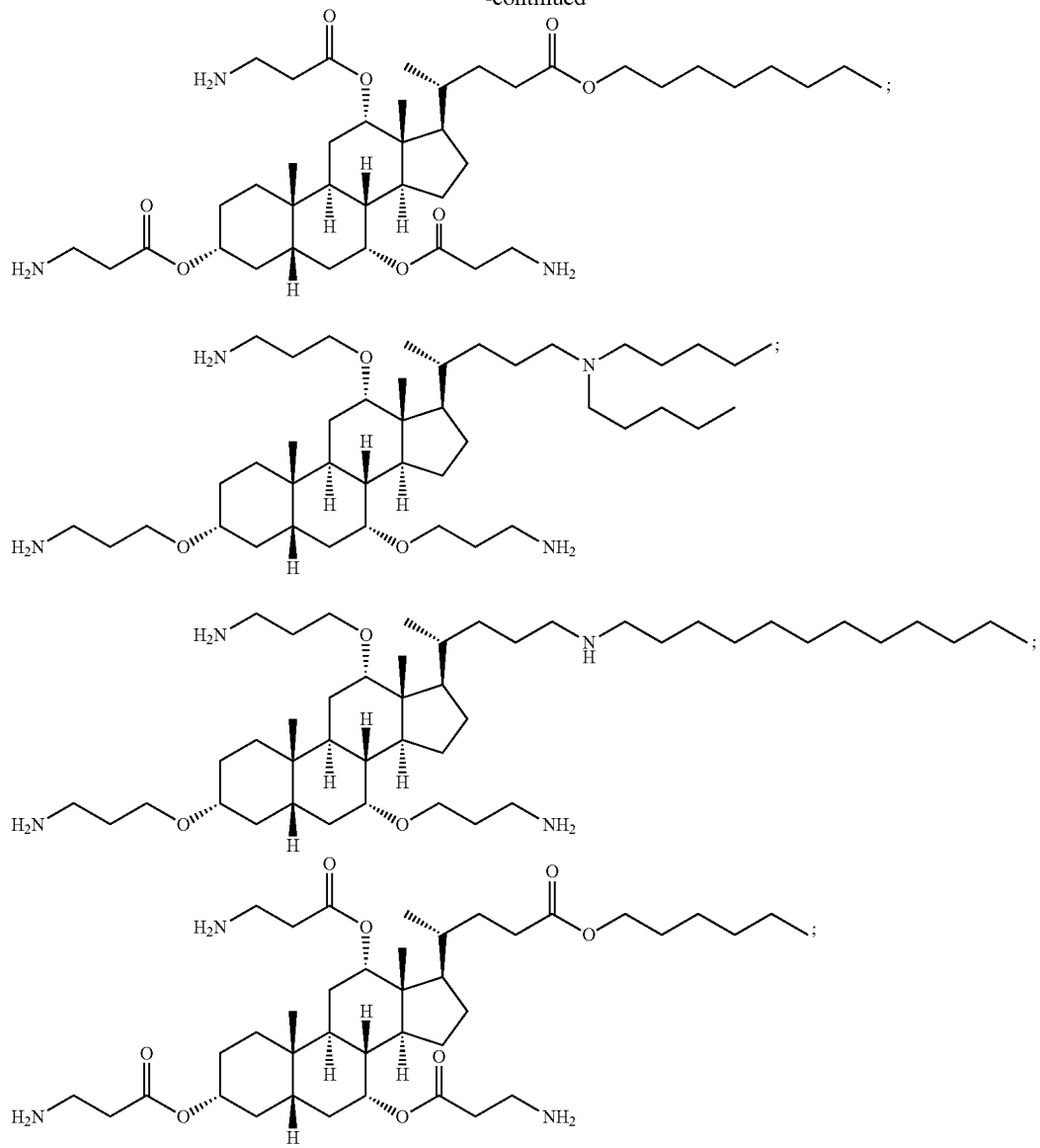

and pharmaceutically acceptable salts thereof.

35. The method of claim 33, wherein the pharmaceutically acceptable device or coating applied to the pharmaceutically acceptable device delivers to the subject an amount of the at least one CSA in a range from about 0.1 µg/g to about 50 µg/g of body weight and/or in a range from about 0.001 mg to about 1000 mg.

36. A method of promoting osteogenesis in a subject in need of treatment for a bone disease or healing a broken bone, comprising:
  identifying a subject in need of treatment for a bone disease or healing a broken bone; and
  administering to the subject an effective amount of at least one cationic steroid antimicrobial (CSA) for promoting osteogenesis selected from the group consisting of:

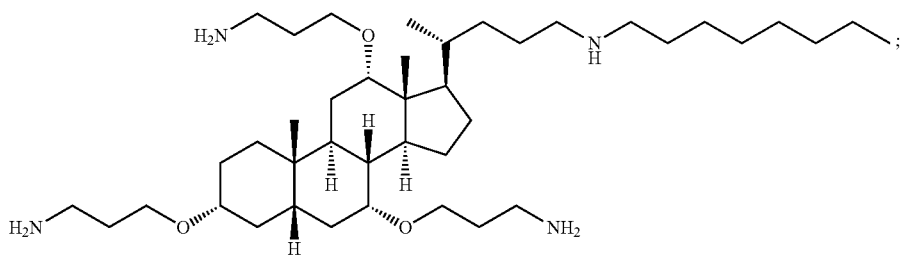

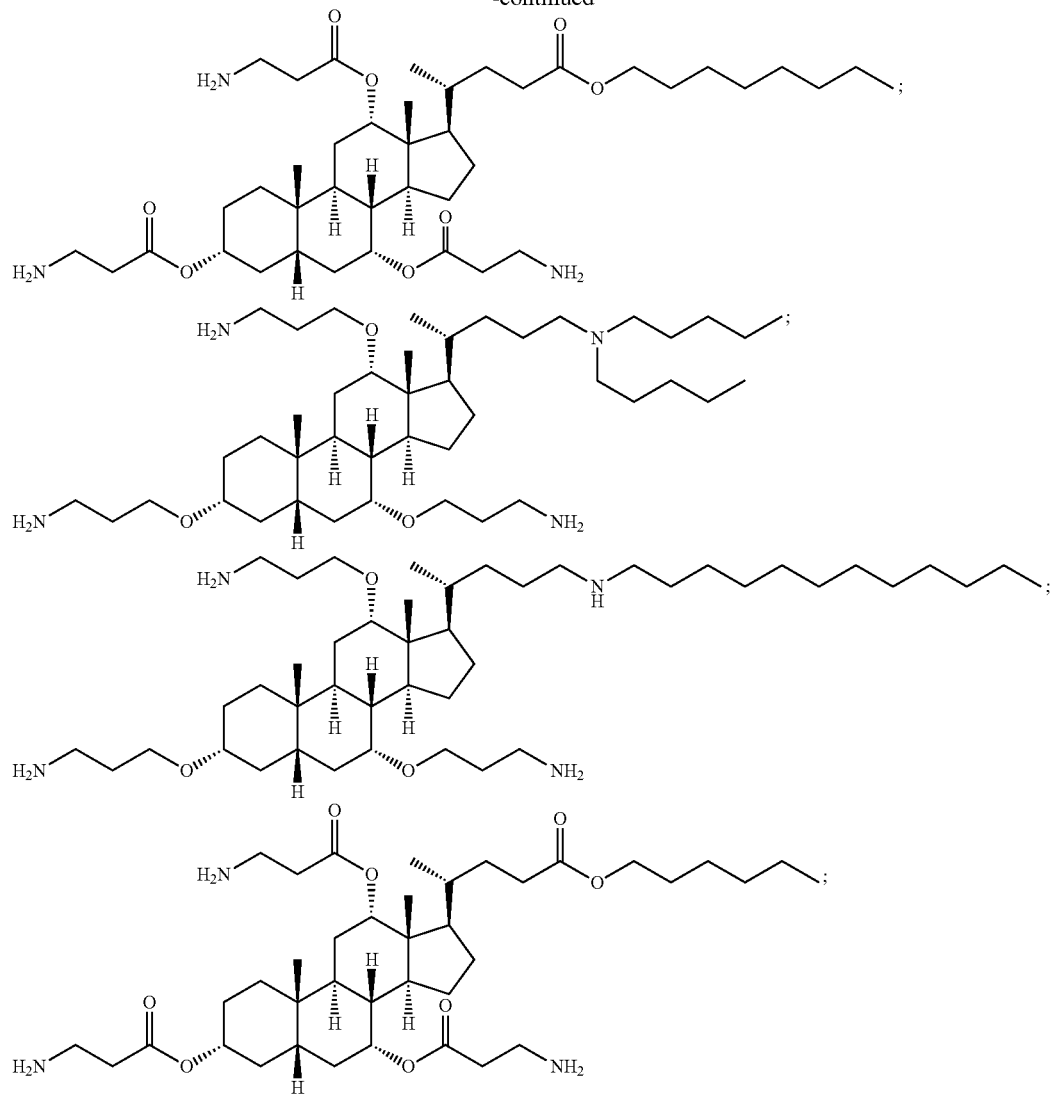
and pharmaceutically acceptable salts thereof.
37. The method of claim 36, wherein the effective amount of at least one CSA is in a range from about 0.1 μg/g to about 50 μg/g of body weight and/or in a range from about 0.001 mg to about 1000 at least one CSA.

UNITED STATES PATENT AND TRADEMARK OFFICE
CERTIFICATE OF CORRECTION

PATENT NO.         : 9,155,746 B2
APPLICATION NO.    : 13/615244
DATED              : October 13, 2015
INVENTOR(S)        : Genberg et al.

It is certified that error appears in the above-identified patent and that said Letters Patent is hereby corrected as shown below:

In the specification

Column 1
Line 56, change "sat" to -- salt --
Line 62, change "sat" to -- salt --

Column 3
Line 65, change "P.G.-HN-HC(Q5)-C(O)—O—" to -- P.G.-HN-HC($Q_5$)-C(O)—O— --

Column 5
Line 11, change "P.G.-HN-HC(Q5)-C(O)—O—" to -- P.G.-HN-HC($Q_5$)-C(O)—O— --

Column 19
Line 29, change "P.G.-HN-HC(Q5)-C(O)—O—" to -- P.G.-HN-HC($Q_5$)-C(O)—O— --

Column 20
Line 37, change "P.G.-HN-HC(Q5)-C(O)—O—" to -- P.G.-HN-HC($Q_5$)-C(O)—O— --

Column 22
Line 5, change "$R_{14}$, $R_{15}$, $R_{16}$," to -- $R_{14}$, $R_{16}$, --

Column 25
Line 39, change "$H_2$N-Hc(Q5)-C(O)—O—" to -- $H_2$N -HC($Q_5$)-C(O)—O— --
Line 40, change "$H_2$N-HC(Q5)-C(O)—N(H)—" to -- $H_2$N -HC($Q_5$)-C(O)—N(H)— --
Line 41, change "P.G.-HN-HC(Q5)-C(O)—O—" to -- P.G.-HN-HC($Q_5$)-C(O)—O— --
Line 50, change "hydroxyl, 10 a" to -- hydroxyl, a --
Line 58, change "$H_2$N-HC(Q5)-C(O)—O—" to -- $H_2$N -HC($Q_5$)-C(O)—O— --
Line 59, change "$H_2$N-HC(Q5)-C(O)—N(H)—" to -- $H_2$N -HC($Q_5$)-C(O)—N(H)— --
Line 60, change "P.G.-HN-HC(Q5)-C(O)—O—" to -- P.G.-HN-HC($Q_5$)-C(O)—O— --

Signed and Sealed this
Twenty-sixth Day of April, 2016

Michelle K. Lee
*Director of the United States Patent and Trademark Office*

In the specification

Line 61, change "Q5" to -- $Q_5$ --

Column 26
Line 5, change "H₂N-HC(Q5)-C(O)—O—" to -- H₂N -HC($Q_5$)-C(O)—O— --
Line 6, change "H₂N-HC(Q5)-C(O)—N(H)—" to -- H₂N -HC($Q_5$)-C(O)—N(H)— --
Line 7, change "P.G.-HN-HC(Q5)-C(O)—O—" to -- P.G.-HN-HC($Q_5$)-C(O)—O— --
Line 43, change "H₂N-HC(Q5)-C(O)—O—" to -- H₂N -HC($Q_5$)-C(O)—O— --
Line 44, change "H₂N-HC(Q5)-C(O)—N(H)—" to -- H₂N -HC($Q_5$)-C(O)—N(H)— --
Line 45, change "P.G.-HN-HC(Q5)-C(O)—O—" to -- P.G.-HN-HC($Q_5$)-C(O)—O— --
Line 61, change "H₂N-HC(Q5)-C(O)—O—" to -- H₂N -HC($Q_5$)-C(O)—O— --
Line 62, change "H₂N-HC(Q5)-C(O)—N(H)—" to -- H₂N -HC($Q_5$)-C(O)—N(H)— --
Line 63, change "P.G.-HN-HC(Q5)-C(O)—O—" to -- P.G.-HN-HC($Q_5$)-C(O)—O— --
Line 64, change "( — )" to -- ($C_1$-$C_{10}$) --

Column 27
Line 12, change "H₂N-HC(Q5)-C(O)—O—" to -- H₂N -HC($Q_5$)-C(O)—O— --
Line 13, change "H₂N-HC(Q5)-C(O)—N(H)—" to -- H₂N -HC($Q_5$)-C(O)—N(H)— --
Line 14, change "P.G.-HN-HC(Q5)-C(O)—O—" to -- P.G.-HN-HC($Q_5$)-C(O)—O— --
Line 14, change "cyanoalkylox" to -- cyanoalkyloxy --
Line 30, change "C3, C7, and C12" to -- $C_3$, $C_7$, and $C_{12}$ --
Line 32, change "C3, C7, and C12" to -- $C_3$, $C_7$, and $C_{12}$ --
Line 39, change "C3, C7, and C12" to -- $C_3$, $C_7$, and $C_{12}$ --
Line 41, change "C3, C7, and C12" to -- $C_3$, $C_7$, and $C_{12}$ --

Column 31
Line 53, change "hydroxypropyl-o-cyclodextrin" to -- hydroxypropyl-O-cyclodextrin --
Line 58, change "hydroxypropyl-o-cyclodextrin" to -- hydroxypropyl-O-cyclodextrin --
Line 59, change "hydroxypropyl-o-cyclodextrin" to -- hydroxypropyl-O-cyclodextrin --
Line 60, change "hydroxypropyl-o-cyclodextrin" to -- hydroxypropyl-O-cyclodextrin --

Column 37
Line 4, change "type pathogenesis" to -- type of pathogenesis --
Line 41, change "ingredient is delivered is administered" to -- ingredient is administered --

Column 39
Line 4, change "housing one" to -- housing of one --
Line 28, change "SABisosciences" to -- SABiosciences --

Column 43
Line 22, change "performed in on multiple" to -- performed in multiple --

CERTIFICATE OF CORRECTION (continued)
U.S. Pat. No. 9,155,746 B2

In the claims

Column 45, Line 17, claim 9 change "osteoporosis, osteomalacia, osteitis" to -- osteoporosis, osteitis --
Column 45, Line 58, claim 12 change "$R_{14}$, $R_{15}$, $R_{16}$," to -- $R_{14}$, $R_{16}$, --
Column 46, Line 22, claim 15 change "alkyoxycarbonylalkyl" to -- alkyloxycarbonylalkyl --